(12) United States Patent
Balaganesan et al.

(10) Patent No.: US 9,450,192 B2
(45) Date of Patent: Sep. 20, 2016

(54) CARBAZOLE DERIVATIVE AND ORGANIC ELECTROLUMINESCENT DEVICES UTILIZING THE SAME AND FABRICATION METHOD THEREOF

(75) Inventors: Banumathy Balaganesan, Taoyuan (TW); Kun-Feng Chiang, Taoyuan (TW); Huang-Ming Guo, Taoyuan (TW); Po-Wei Hsu, Taoyuan (TW)

(73) Assignee: E-RAY OPTOELECTRONICS TECHNOLOGY, Chung-Li (TW)

( * ) Notice: Subject to any disclaimer, the term of this patent is extended or adjusted under 35 U.S.C. 154(b) by 142 days.

(21) Appl. No.: 13/310,899

(22) Filed: Dec. 5, 2011

(65) Prior Publication Data

US 2012/0175598 A1 Jul. 12, 2012

Related U.S. Application Data

(60) Provisional application No. 61/420,016, filed on Dec. 6, 2010.

(51) Int. Cl.
*H01L 51/54* (2006.01)
*C07D 209/88* (2006.01)
(Continued)

(52) U.S. Cl.
CPC ......... *H01L 51/0072* (2013.01); *C07D 209/88* (2013.01); *C07D 403/04* (2013.01); *C07D 403/12* (2013.01); *C07D 403/14* (2013.01); *C07D 487/04* (2013.01); *C07D 491/048* (2013.01); *C09K 11/06* (2013.01); *H05B 33/14* (2013.01); *C09K 2211/1022* (2013.01); *C09K 2211/1029* (2013.01); *C09K 2211/1059* (2013.01); *H01L 51/0061* (2013.01); *H01L 51/0081* (2013.01); *H01L 51/0085* (2013.01); *H01L 51/5016* (2013.01); *H01L 51/5056* (2013.01); *H01L 51/5072* (2013.01); *H01L 51/5096* (2013.01)

(58) Field of Classification Search
None
See application file for complete search history.

(56) References Cited

U.S. PATENT DOCUMENTS

2005/0095458 A1* 5/2005 Kim et al. ............... 428/690
2005/0252602 A1* 11/2005 Tateishi ................... 156/230

(Continued)

*Primary Examiner* — J. L. Yang
(74) *Attorney, Agent, or Firm* — Amin, Turocy & Watson, LLP

(57) ABSTRACT

The present invention provides a carbazole derivative of formula (I) for an organic electroluminescent device:

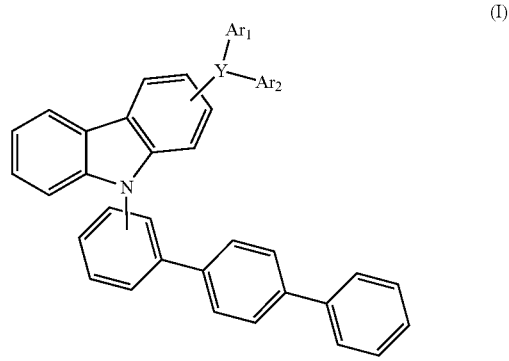

(I)

wherein Y represents a heteroatom selected from N, O, P, S, or a bicyclic or tricyclic heterocyclic ring; and
$Ar_1$ and $Ar_2$ each independently represent an alkyl or aryl substituted or unsubstituted aromatic hydrocarbon, or an alkyl or aryl substituted or unsubstituted heterocyclic aromatic hydrocarbon.

18 Claims, 12 Drawing Sheets

(51) Int. Cl.
*H01L 51/56* (2006.01)
*C07D 491/048* (2006.01)
*C09K 11/06* (2006.01)
*C07D 403/12* (2006.01)
*C07D 487/04* (2006.01)
*H01L 51/00* (2006.01)
*C07D 403/04* (2006.01)
*C07D 403/14* (2006.01)
*H05B 33/14* (2006.01)
*H01L 51/50* (2006.01)

(56) References Cited

U.S. PATENT DOCUMENTS

2007/0231503 A1* 10/2007 Hwang et al. .................. 428/1.1
2008/0124572 A1* 5/2008 Mizuki et al. .................. 428/690
2008/0284328 A1* 11/2008 Nakashima et al. ........... 313/506

* cited by examiner

CARBAZOLE DERIVATIVE AND ORGANIC ELECTROLUMINESCENT DEVICES UTILIZING THE SAME AND FABRICATION METHOD THEREOF

BACKGROUND OF THE INVENTION

1. Field of the Invention

The present invention relates to a material for organic electroluminescence devices and an organic electroluminescence device using the said material, and more particularly to a material for organic electroluminescence (EL) devices providing an electroluminescence device exhibiting a high luminous efficiency, sufficiently reduced driving voltage, high thermal resistance and has long lifetime.

2. Prior Art

There has been an increasing interest in developing novel organic materials that cater to organic light emitting devices (OLEDs). Such devices are commercially attractive because they offer the cost-advantageous fabrication of high density pixeled displays exhibiting brilliant luminance with long life times, high efficiency, low driving voltages and wide color range.

A typical OLED comprises at least one organic emissive layer sandwiched between an anode and a cathode. When a current is applied, the anode injects holes and the cathode injects electrons into the organic layer(s). The injected holes and electrons each migrate toward the oppositely charged electrode. When an electron and hole localize on the same molecule, an "exciton" which is a localized electron-hole pair having an excited energy state, is formed. Light is emitted when the exciton relaxes through a photoemissive mechanism. To improve the charge transport capabilities and also the luminous efficiency of such devices, additional layers around the emissive layer, such as an electron transport layer and/or a hole transport layer, or an electron blocking and/or hole blocking layer(s) have been incorporated. Doping the host material with another material (guest) has been well demonstrated in literature to enhance the device performance and to tune the chromaticity. Several OLED materials and device configurations are described in U.S. Pat. Nos. 4,769,292, 5,844,363, 5,707,745, 6,596,415 and 6,465,115, which are incorporated herein by reference in their entirety.

The reason for manufacturing an organic EL display with a multi-layered thin film structure includes stabilization of the interfaces between the electrodes and the organic layers. In addition, in organic materials, the mobility of electrons and holes significantly differ, and thus, if appropriate hole transportation and electron transportation layers are used, holes and electrons can be efficiently transferred to the luminescent layer. Also, if the density of the holes and electrons are balanced in the emitting layer, luminous efficiency can be increased. The proper combination of organic layers described above can enhance the device efficiency and lifetime. However, it has been very difficult to find an organic material that satisfies all the requirements for use in practical display applications.

The most important factors to determine luminous efficiency, lifetime in an organic EL device are the appropriate matching of the singlet or triplet energy levels, balanced mobility of electrons and holes, stability of the material during evaporation and thin film morphology, thus leading to the requirement of materials with significantly improved characteristics.

SUMMARY OF THE INVENTION

To achieve the above objects, the present inventors have designed and synthesized carbazole derivatives containing terphenyl group, experimentally fabricated organic electroluminescent devices using these compounds, and evaluated the device characteristics, to complete the present invention.

That is, the above objects have been achieved by providing a carbazole derivative containing terphenyl group, represented by the general formula (I), and an organic electroluminescent device comprising the said compound contained as a constituent material in one of the organic layers:

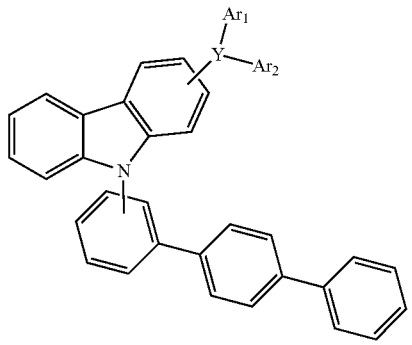

(I)

wherein Y represents a heteroatom selected from N, O, P, S, or a bicyclic or tricyclic heterocyclic ring; and $Ar_1$ and $Ar_2$ each independently represent an alkyl or aryl substituted or unsubstituted aromatic hydrocarbon, or an alkyl or aryl substituted or unsubstituted heterocyclic aromatic hydrocarbon Further, the present invention provides a process for producing the specific compounds represented by the general formula (I).

In one aspect, the present invention provides an organic electroluminescent device, comprising a substrate; an electrode; and a sandwich structure formed between the substrate and electrode, wherein said sandwich structure has a hole transporting layer, an electron transporting layer, and a light emitting layer sandwiched between the hole transporting layer and electron transporting layer.

The compound according to the present invention represented by the general formula (I), is capable of being made into an amorphous thin film by means of vacuum deposition method or spin coating method, for the organic electroluminescent devices of the invention.

For example, the organic electroluminescent device utilizes the aforementioned compound represented by the general formula (I), in hole transport layer or hole injection layer or in the emitting layer.

Another aspect of this invention relates to an organic electroluminescent device that utilizes the aforementioned compound represented by the general formula (I), in one of the layers described as electron transport layer or hole block layer or electron block layer. Generally, one layer of the organic electroluminescent device contains at least one compound of the carbazole derivative of the invention.

Yet another aspect of this invention relates to an organic electroluminescent device that utilizes the aforementioned compound represented by the general formula (I), in the light emitting layer used in combination with a fluorescent or a phosphorescent emitter.

Organic electroluminescent devices comprising the compound of the invention represented by the general formula (I), employed in any of the organic layers described above, exhibit a reduced driving voltage with high efficiency, longer lifetime and better thermal stability.

The present invention provides a method for forming an organic electroluminescent device, comprising:
  forming a hole injection layer on a substrate;
  forming a hole transport layer on the hole injecting layer;
  forming a light emitting layer on the hole transport layer having a phosphorescent dopant and at least one compound of the carbazole derivative of the invention;
  forming a electron transporting layer on the light emitting layer;
  forming a electron injection layer on the electron transporting layer; and
  forming a electrode on the electron injection layer.

In addition, by using the organic compound of the present invention represented by the general formula (I), employed in any of the organic layers described above, it becomes possible to provide an organic electroluminescent device which can emit white light.

DETAILED DESCRIPTION OF THE PREFERRED EMBODIMENTS

Figure 1:
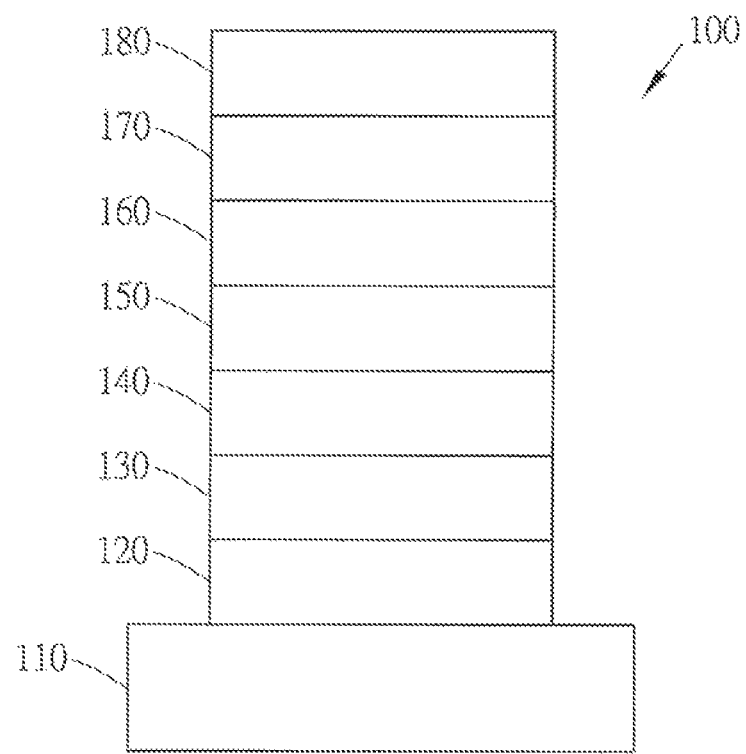
FIG. 1 is a cross-sectional view illustrating one example of an organic light emitting according to an embodiment of the present invention.

The detailed description of the present invention is illustrated by the following specific examples. Persons skilled in the art can conceive the other advantages and effects of the present invention based on the disclosure contained in the specification of the present invention.

A compound for an organic electroluminescent device according to this invention is represented by the general formula (I). Preferable examples of the compounds represented by general formula (I) are shown in Table 1, but not limited thereto.

In the general formula (I), Y represents a heteroatom selected from N, O, P, S, or a bicyclic or tricyclic heterocyclic ring; and $Ar_1$ and $Ar_2$ each independently represent an alkyl/aryl substituted or unsubstituted aromatic hydrocarbon, or an alkyl/aryl substituted or unsubstituted heterocyclic aromatic hydrocarbon. In one embodiment, Y represents a bicyclic heterocyclic ring fused with the carbazole.

TABLE 1

Compound
1-1

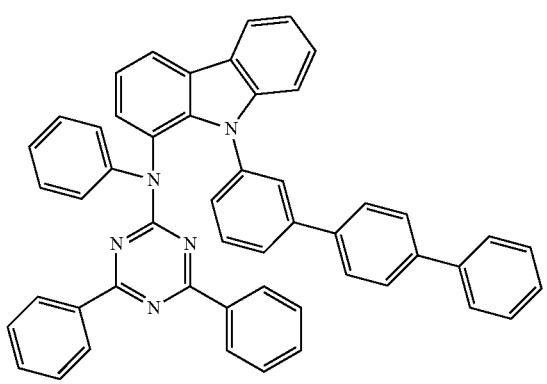 [SMILES: c1ccc(-c2ccc(-c3cccc(-n4c5ccccc5c5cccc(N(c6ccccc6)c6nc(-c7ccccc7)nc(-c7ccccc7)n6)c54)c3)cc2)cc1]

TABLE 1-continued
Compound 1-2
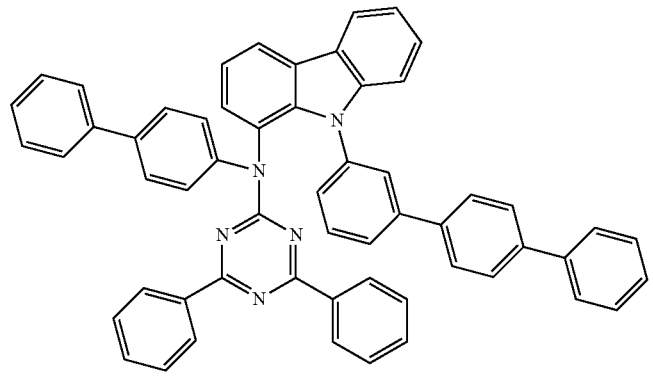 [SMILES: c1ccc(-c2ccc(-c3cccc(-n4c5ccccc5c5cccc(N(c6ccc(-c7ccccc7)cc6)c6nc(-c7ccccc7)nc(-c7ccccc7)n6)c54)c3)cc2)cc1]
Compound 1-3
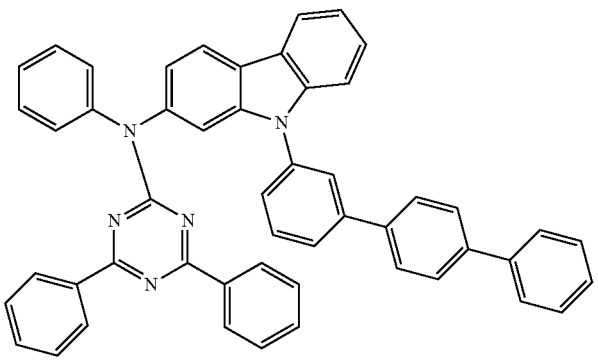 [SMILES: c1ccc(-c2ccc(-c3cccc(-n4c5ccccc5c5ccc(N(c6ccccc6)c6nc(-c7ccccc7)nc(-c7ccccc7)n6)cc54)c3)cc2)cc1]
Compound 1-4
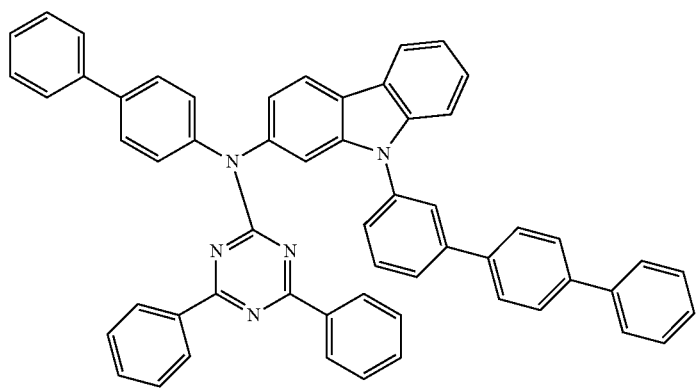 [SMILES: c1ccc(-c2ccc(-c3cccc(-n4c5ccccc5c5ccc(N(c6ccc(-c7ccccc7)cc6)c6nc(-c7ccccc7)nc(-c7ccccc7)n6)cc54)c3)cc2)cc1]
Compound 1-5
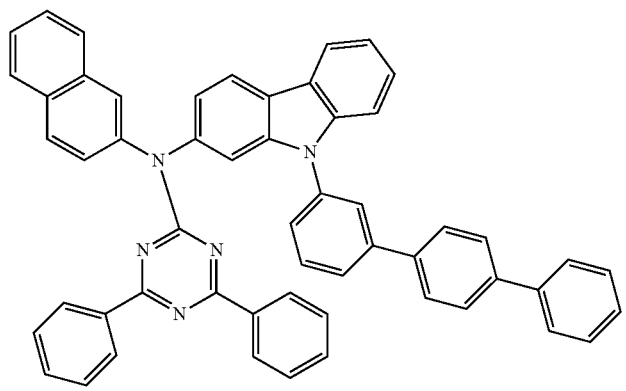 [SMILES: c1ccc(-c2ccc(-c3cccc(-n4c5ccccc5c5ccc(N(c6ccc7ccccc7c6)c6nc(-c7ccccc7)nc(-c7ccccc7)n6)cc54)c3)cc2)cc1]

TABLE 1-continued
Compound
1-6
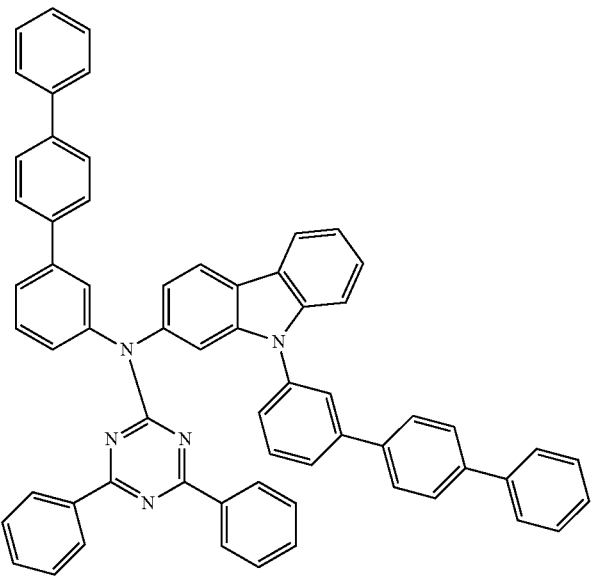 [SMILES: c1ccc(-c2ccc(-c3cccc(N(c4ccc5c6ccccc6n(-c6cccc(-c7ccc(-c8ccccc8)cc7)c6)c5c4)c4nc(-c5ccccc5)nc(-c5ccccc5)n4)c3)cc2)cc1]
Compound
1-7
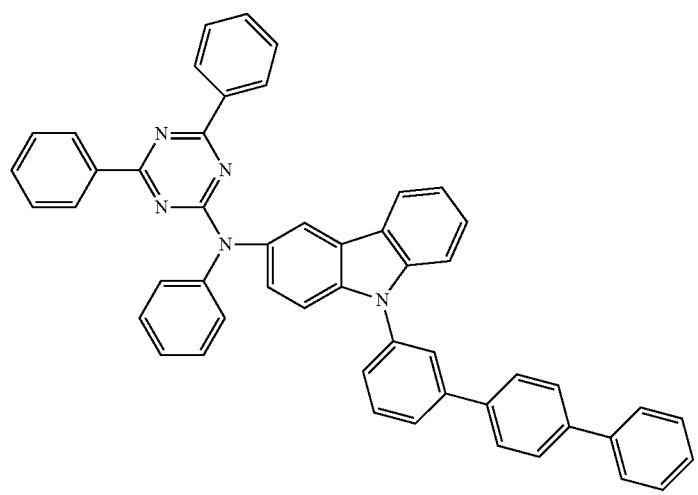 [SMILES: c1ccc(-c2ccc(-c3cccc(-n4c5ccccc5c5cc(N(c6ccccc6)c6nc(-c7ccccc7)nc(-c7ccccc7)n6)ccc54)c3)cc2)cc1]
Compound
1-8
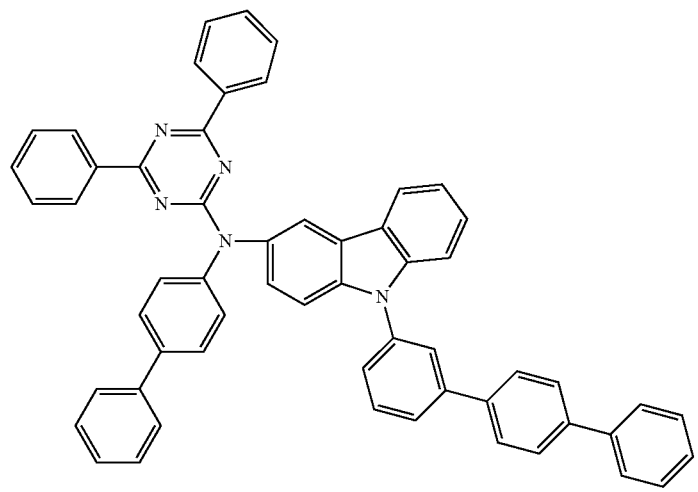 [SMILES: c1ccc(-c2ccc(-c3cccc(-n4c5ccccc5c5cc(N(c6ccc(-c7ccccc7)cc6)c6nc(-c7ccccc7)nc(-c7ccccc7)n6)ccc54)c3)cc2)cc1]

TABLE 1-continued
| Compound 1-9 | 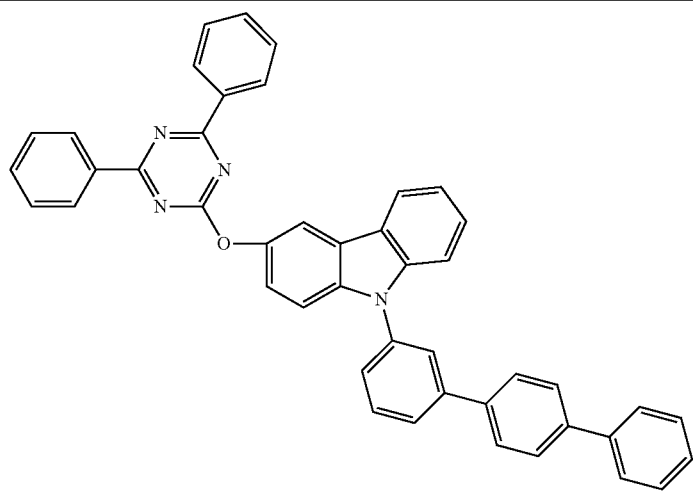 |
| --- | --- |
| Compound 1-10 | 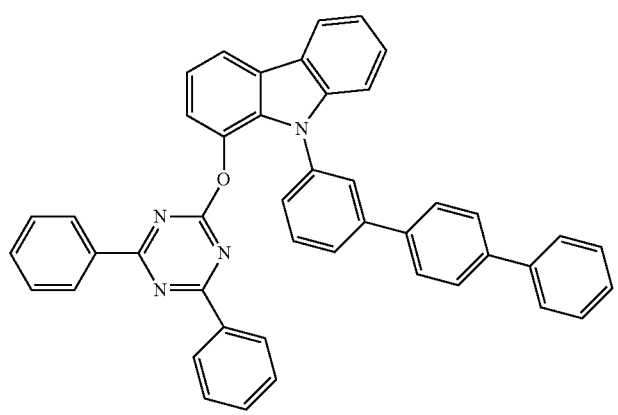 [SMILES: c1ccc(-c2ccc(-c3cccc(-n4c5ccccc5c5cccc(Oc6nc(-c7ccccc7)nc(-c7ccccc7)n6)c54)c3)cc2)cc1] |
| Compound 1-11 | 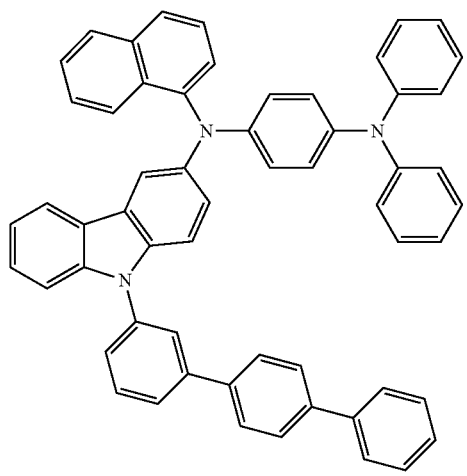 [SMILES: c1ccc(-c2ccc(-c3cccc(-n4c5ccccc5c5cc(N(c6ccc(N(c7ccccc7)c7ccccc7)cc6)c6cccc7ccccc67)ccc54)c3)cc2)cc1] |

TABLE 1-continued
Compound
1-12
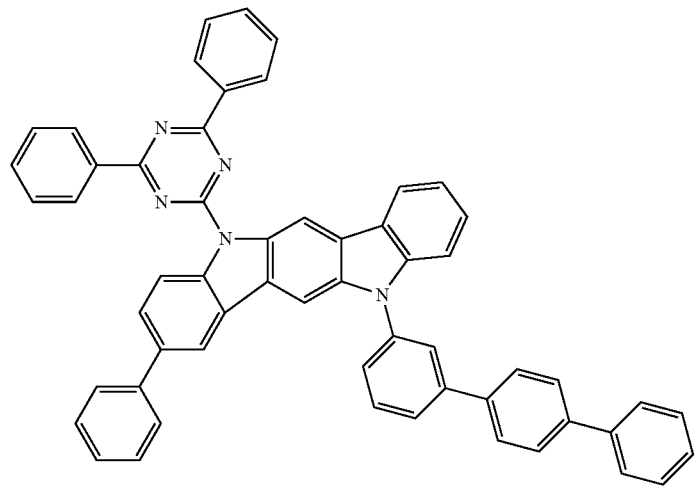 [SMILES: c1ccc(-c2ccc(-c3cccc(-n4c5ccccc5c5cc6c(cc54)c4cc(-c5ccccc5)ccc4n6-c4nc(-c5ccccc5)nc(-c5ccccc5)n4)c3)cc2)cc1]
Compound
1-13
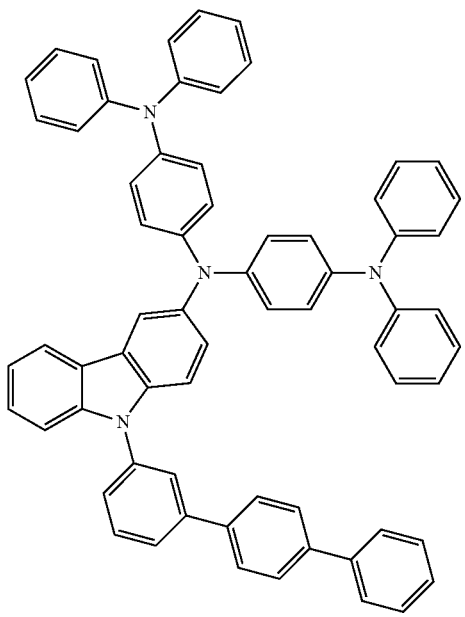 [SMILES: c1ccc(-c2ccc(-c3cccc(-n4c5ccccc5c5cc(N(c6ccc(N(c7ccccc7)c7ccccc7)cc6)c6ccc(N(c7ccccc7)c7ccccc7)cc6)ccc54)c3)cc2)cc1]
Compound
1-14
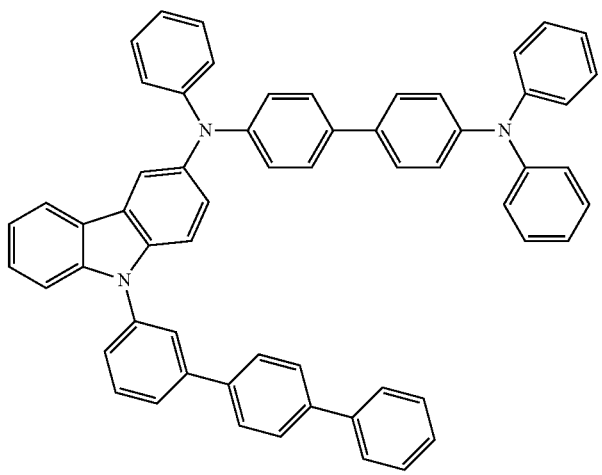 [SMILES: c1ccc(-c2ccc(-c3cccc(-n4c5ccccc5c5cc(N(c6ccccc6)c6ccc(-c7ccc(N(c8ccccc8)c8ccccc8)cc7)cc6)ccc54)c3)cc2)cc1]

TABLE 1-continued
Compound 1-15
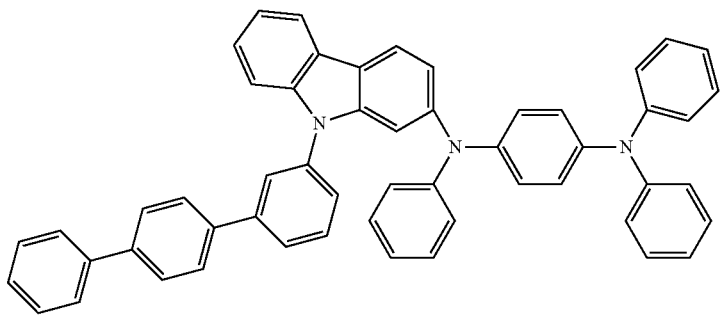 [SMILES: c1ccc(-c2ccc(-c3cccc(-n4c5ccccc5c5ccc(N(c6ccccc6)c6ccc(N(c7ccccc7)c7ccccc7)cc6)cc54)c3)cc2)cc1]
Compound 1-16
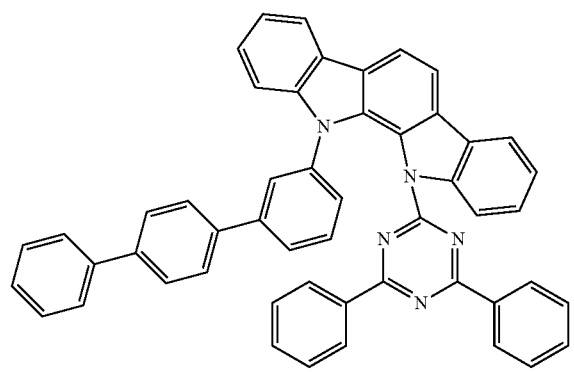 [SMILES: c1ccc(-c2ccc(-c3cccc(-n4c5ccccc5c5ccc6c7ccccc7n(-c7nc(-c8ccccc8)nc(-c8ccccc8)n7)c6c54)c3)cc2)cc1]
Compound 1-17
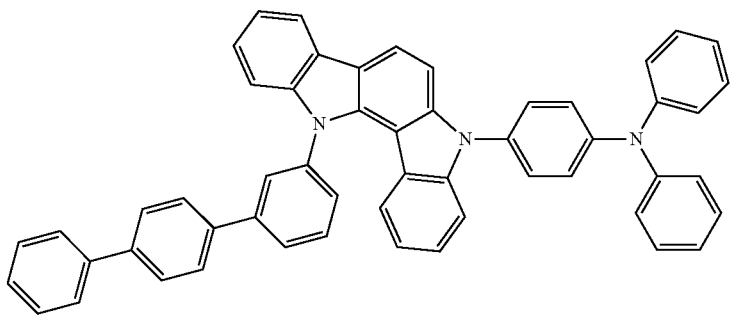 [SMILES: c1ccc(-c2ccc(-c3cccc(-n4c5ccccc5c5ccc6c(c7ccccc7n6-c6ccc(N(c7ccccc7)c7ccccc7)cc6)c54)c3)cc2)cc1]
Compound 1-18
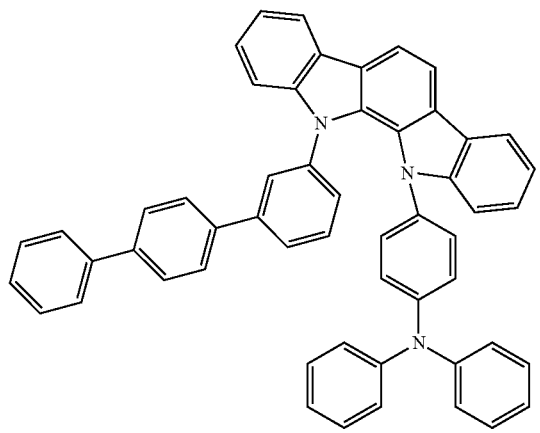 [SMILES: c1ccc(-c2ccc(-c3cccc(-n4c5ccccc5c5ccc6c7ccccc7n(-c7ccc(N(c8ccccc8)c8ccccc8)cc7)c6c54)c3)cc2)cc1]

TABLE 1-continued
Compound
1-19
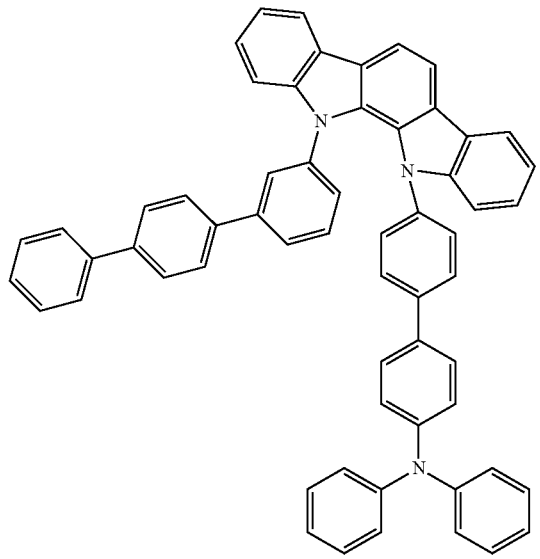 [SMILES: c1ccc(-c2ccc(-c3cccc(-n4c5ccccc5c5ccc6c7ccccc7n(-c7ccc(-c8ccc(N(c9ccccc9)c9ccccc9)cc8)cc7)c6c54)c3)cc2)cc1]
Compound
1-20
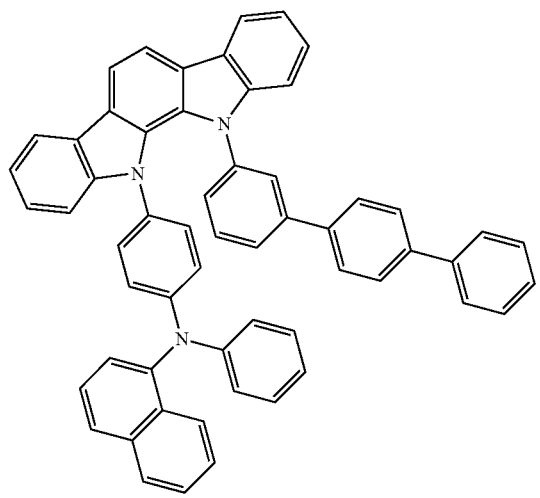 [SMILES: c1ccc(-c2ccc(-c3cccc(-n4c5ccccc5c5ccc6c7ccccc7n(-c7ccc(N(c8ccccc8)c8cccc9ccccc89)cc7)c6c54)c3)cc2)cc1]
Compound
1-21
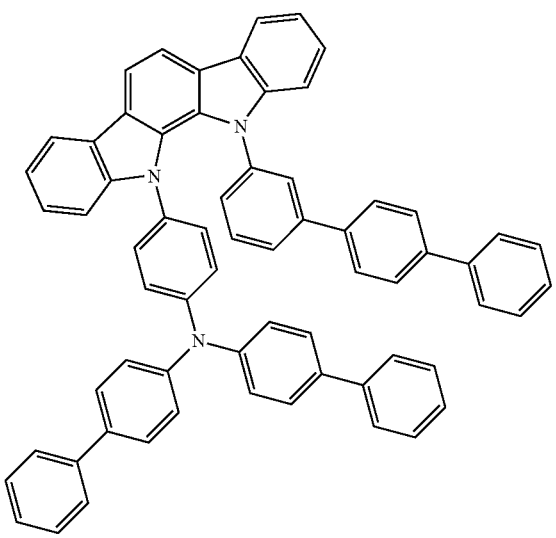 [SMILES: c1ccc(-c2ccc(-c3cccc(-n4c5ccccc5c5ccc6c7ccccc7n(-c7ccc(N(c8ccc(-c9ccccc9)cc8)c8ccc(-c9ccccc9)cc8)cc7)c6c54)c3)cc2)cc1]

TABLE 1-continued
Compound 1-22
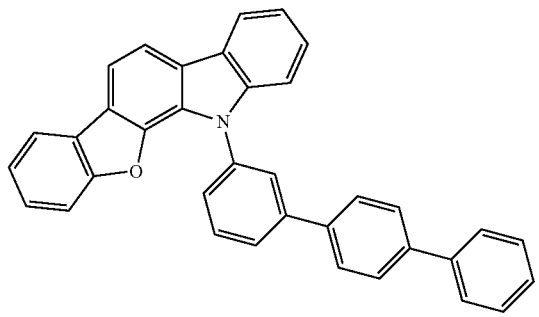 [SMILES: c1ccc(-c2ccc(-c3cccc(-n4c5ccccc5c5ccc6c7ccccc7oc6c54)c3)cc2)cc1]
Compound 1-23
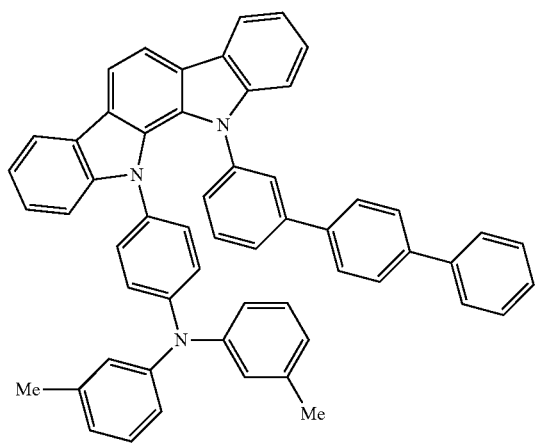 [SMILES: Cc1cccc(N(c2ccc(-n3c4ccccc4c4ccc5c6ccccc6n(-c6cccc(-c7ccc(-c8ccccc8)cc7)c6)c5c43)cc2)c2cccc(C)c2)c1]
Compound 1-24
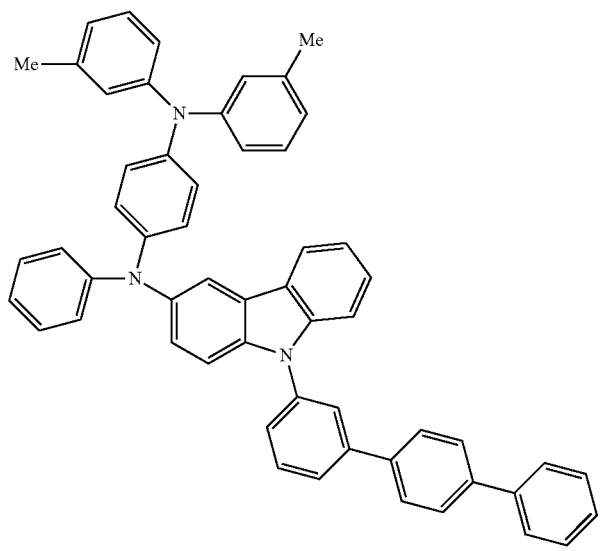 [SMILES: Cc1cccc(N(c2ccc(N(c3ccccc3)c3ccc4c(c3)c3ccccc3n4-c3cccc(-c4ccc(-c5ccccc5)cc4)c3)cc2)c2cccc(C)c2)c1]

TABLE 1-continued
Compound 1-25
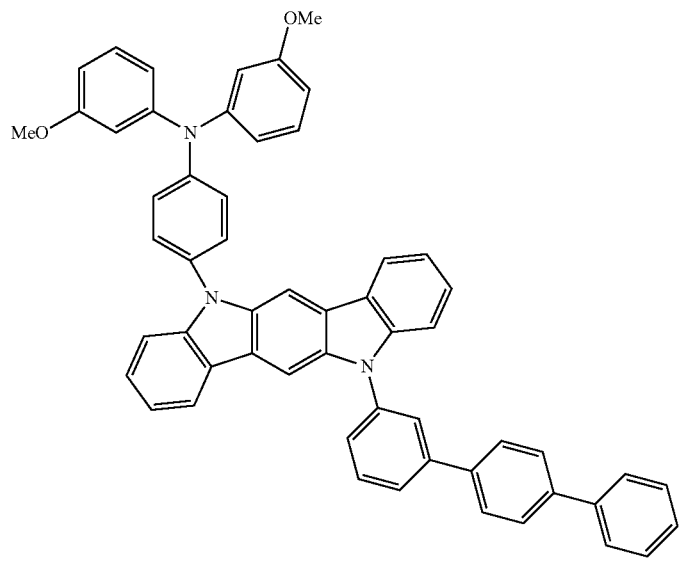 [SMILES: COc1cccc(N(c2ccc(-n3c4ccccc4c4cc5c(cc43)c3ccccc3n5-c3cccc(-c4ccc(-c5ccccc5)cc4)c3)cc2)c2cccc(OC)c2)c1]
Compound 1-26
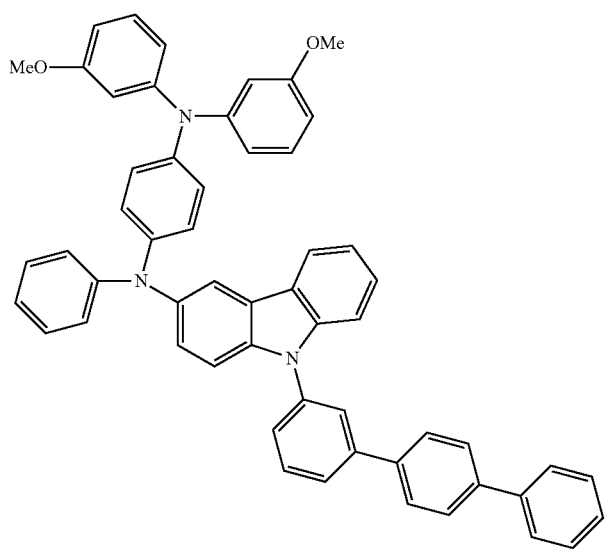 [SMILES: COc1cccc(N(c2ccc(N(c3ccccc3)c3ccc4c(c3)c3ccccc3n4-c3cccc(-c4ccc(-c5ccccc5)cc4)c3)cc2)c2cccc(OC)c2)c1]
Compound 1-27
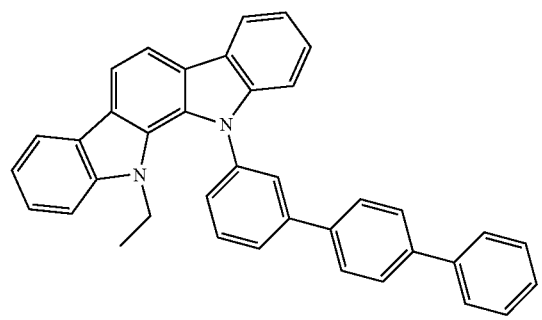 [SMILES: CCn1c2ccccc2c2ccc3c4ccccc4n(-c4cccc(-c5ccc(-c6ccccc6)cc5)c4)c3c21]

TABLE 1-continued
Compound 1-28
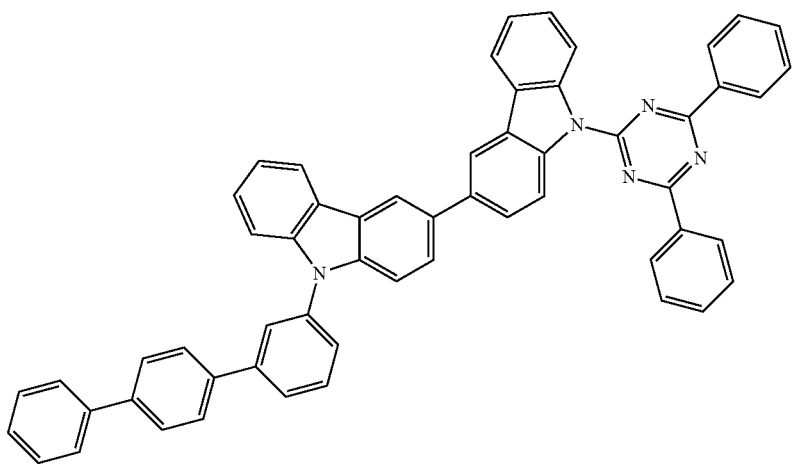 [SMILES: c1ccc(-c2ccc(-c3cccc(-n4c5ccccc5c5cc(-c6ccc7c(c6)c6ccccc6n7-c6nc(-c7ccccc7)nc(-c7ccccc7)n6)ccc54)c3)cc2)cc1]
Compound 1-29
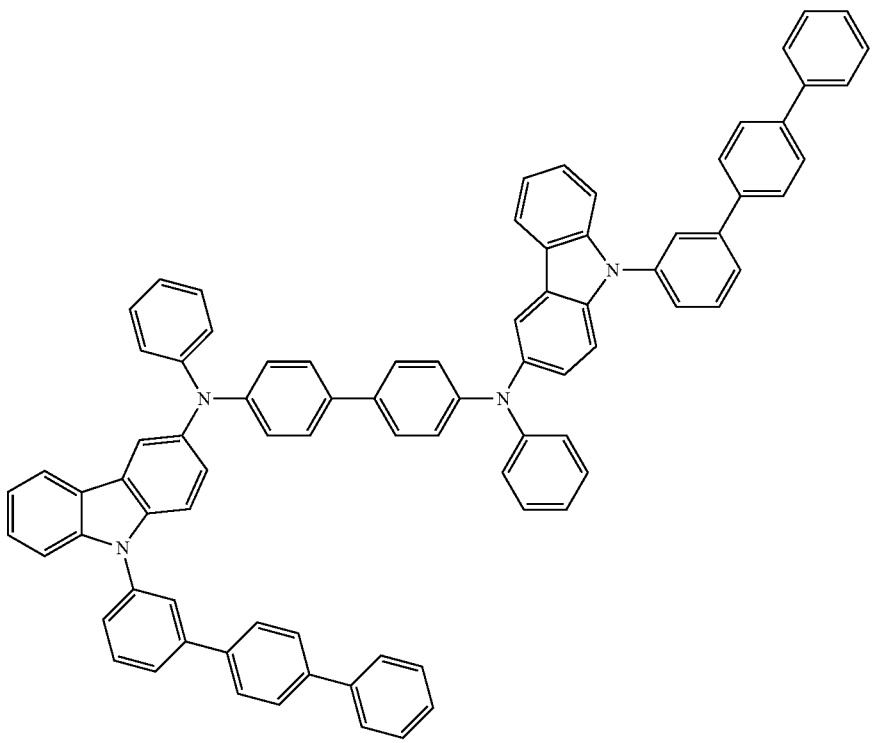 [SMILES: c1ccc(-c2ccc(-c3cccc(-n4c5ccccc5c5cc(N(c6ccccc6)c6ccc(-c7ccc(N(c8ccccc8)c8ccc9c(c8)c8ccccc8n9-c8cccc(-c9ccc(-c%10ccccc%10)cc9)c8)cc7)cc6)ccc54)c3)cc2)cc1]
Compound 1-30
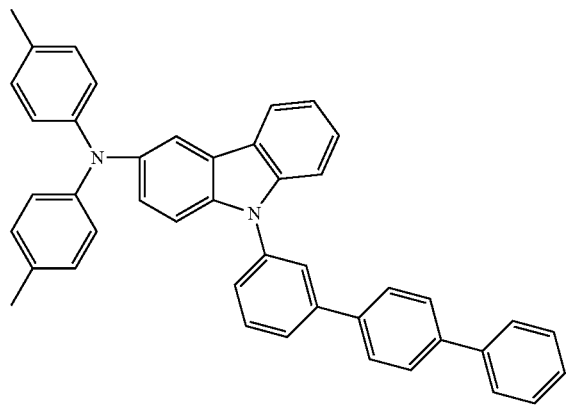 [SMILES: Cc1ccc(N(c2ccc(C)cc2)c2ccc3c(c2)c2ccccc2n3-c2cccc(-c3ccc(-c4ccccc4)cc3)c2)cc1]

TABLE 1-continued
Compound 1-31
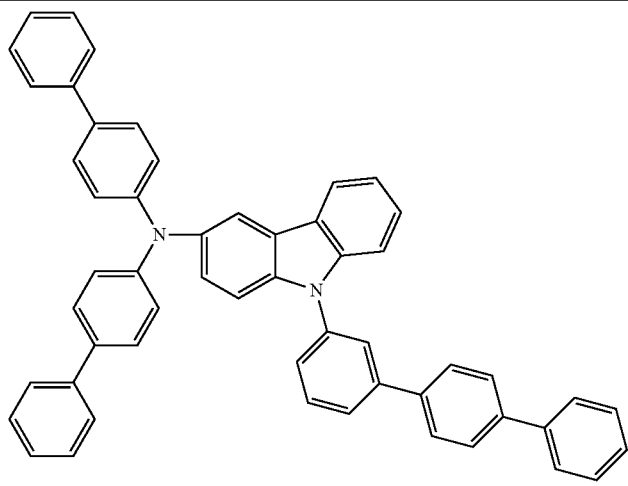
Compound 1-32
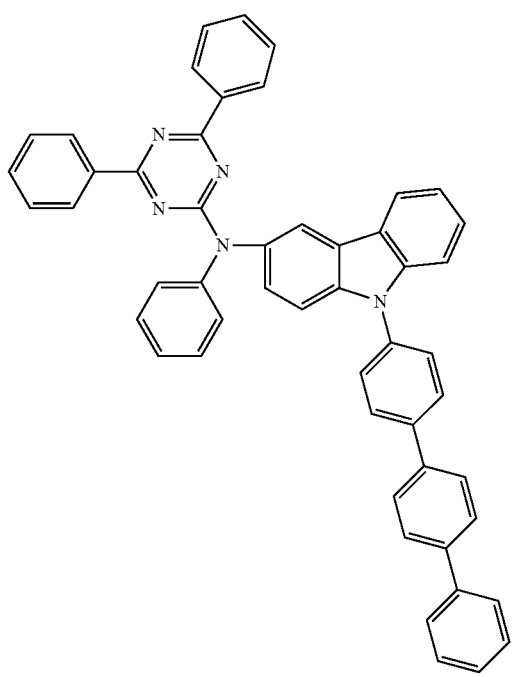 [SMILES: c1ccc(-c2ccc(-c3ccc(-n4c5ccccc5c5cc(N(c6ccccc6)c6nc(-c7ccccc7)nc(-c7ccccc7)n6)ccc54)cc3)cc2)cc1]
Exemplary compounds 1-1 to 1-32, represented by formula (I), may be prepared by, but not limited to, a sequence of reactions as shown in the synthetic schemes 1-3.
Synthetic Scheme 1:
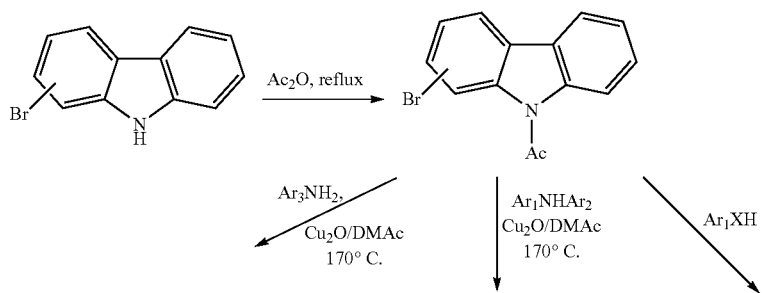

25
26
-continued
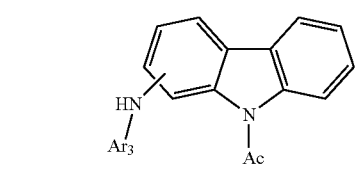 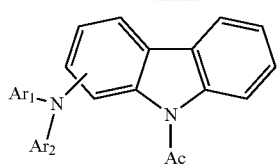 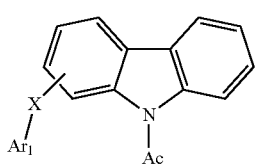
X = O, S
↓ ↓ KOH, THF/MeOH reflux ↓ KOH, THF/MeOH reflux
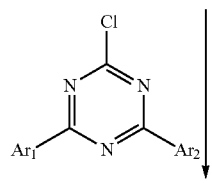
↓
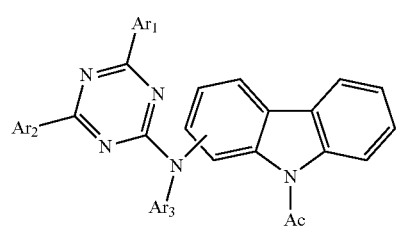 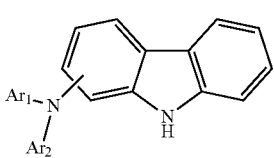 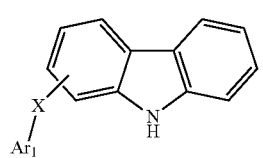
X = O, S
↓ KOH, THF/MeOH reflux ↓ Pd(dba)$_2$, K$_3$PO$_4$ toluene, reflux ↓ Pd(dba)$_2$, K$_3$PO$_4$ toluene, reflux
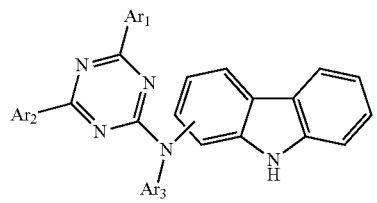 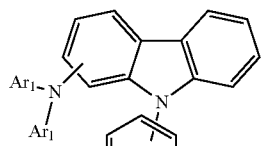 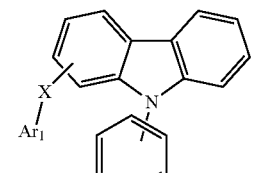
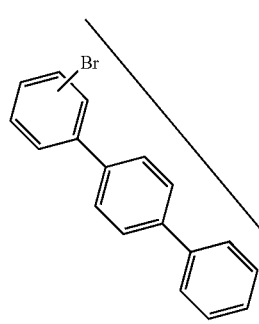
Pd(dba)$_2$, K$_3$PO$_4$ toluene, reflux
↓

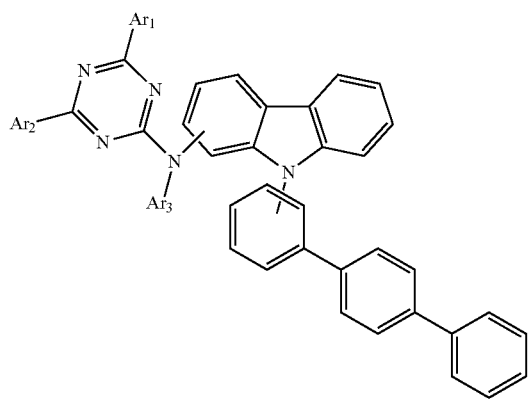

In the Scheme 1 $Ar_1$, $Ar_2$, $Ar_3$ each independently represent an alkyl or aryl substituted or unsubstituted aromatic group, or an alkyl or aryl substituted or unsubstituted heterocyclic group; Also, X may represent O or S.

Synthetic Scheme 2:

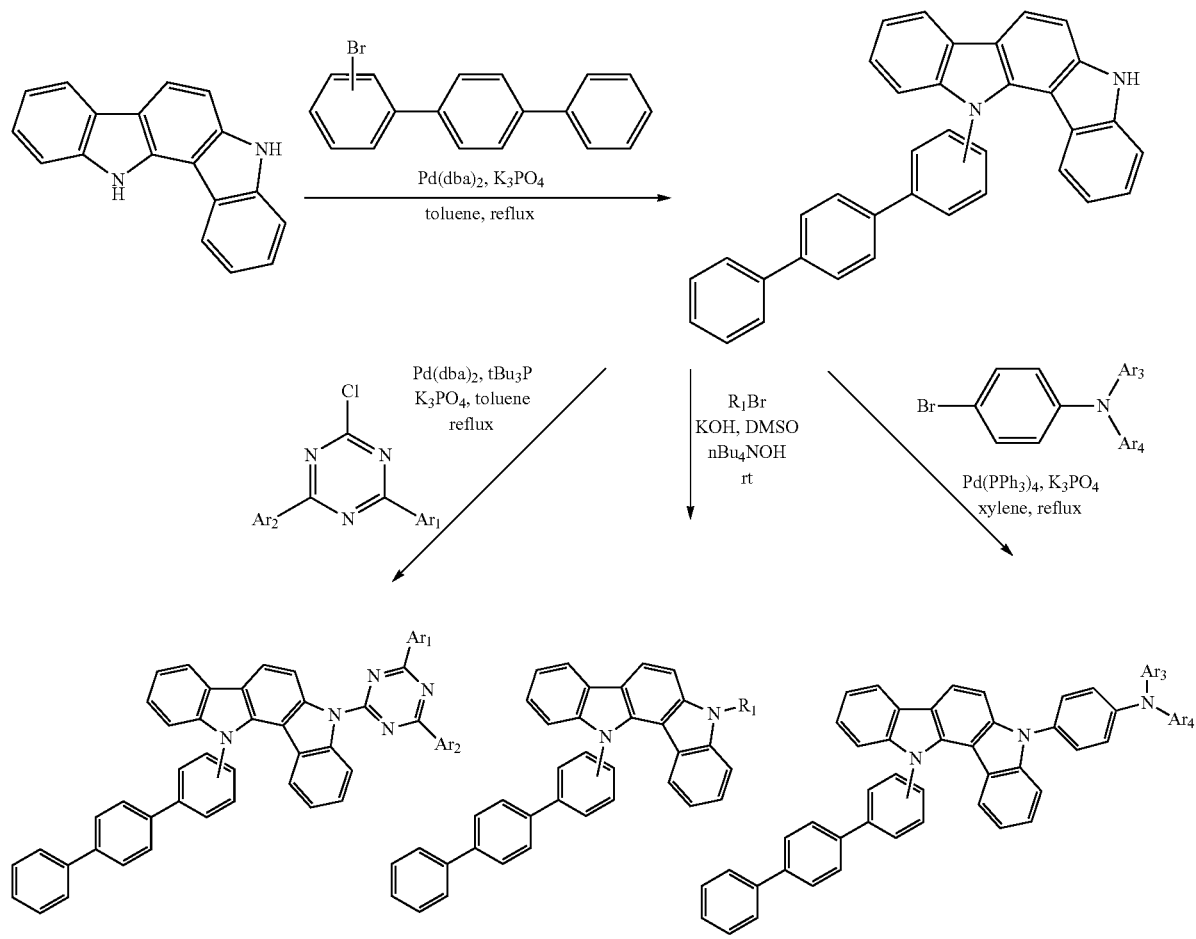

In the Scheme 2 $Ar_1$, $Ar_2$, $Ar_3$, $Ar_4$ each independently represent an alkyl or aryl substituted or unsubstituted aromatic group, or an alkyl or aryl substituted or unsubstituted heterocyclic group; Also, $R_1$ may represent an alkyl group from selected from C1-C16.

Synthesis Scheme 3:

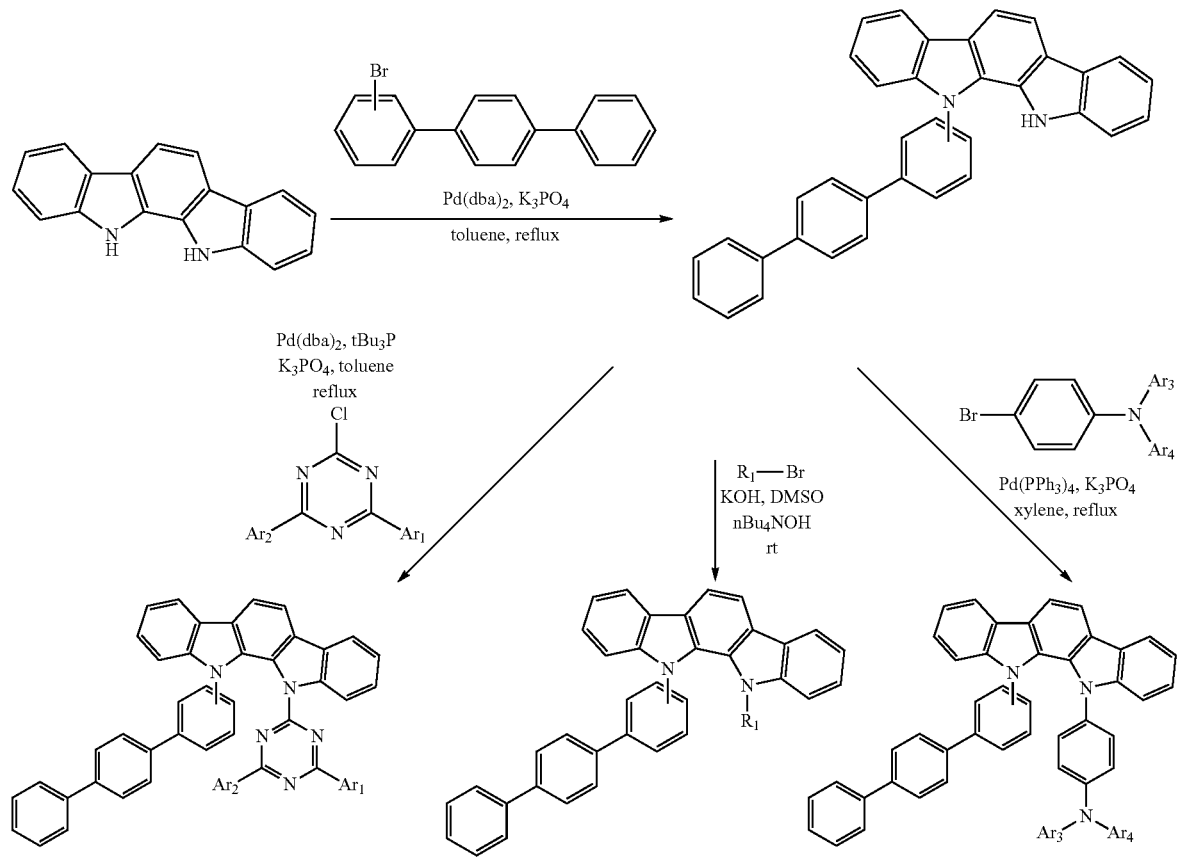

The organic electroluminescent device of this invention has at least one light emitting layer disposed between an anode and a cathode piled one upon another on a substrate, and the light emitting layer includes a phosphorescent dopant and the aforementioned compound represented by formulae (I) (including compound 1-1 to 1-32) as a host material. It is preferable that a hole injecting/transporting layer is disposed between the anode and the light emitting layer and an electron injecting/transporting layer is disposed between the cathode and the light emitting layer. It is also preferable that either a hole blocking layer is disposed between the light emitting layer and the electron injecting/transporting layer or an electron blocking layer is disposed between the hole injecting/transporting layer and the light emitting layer.

Further, the compounds represented by any of formulae (I) may be used in the electron injecting/transporting layer or hole blocking layer and/or electron blocking layer.

Phosphorescent dopants to be used in the light emitting layer are preferably organic metal complexes containing at least one metal selected from ruthenium, rhodium, palladium, silver, rhenium, osmium, iridium, platinum, and gold. Such organic metal complexes are known in the aforementioned patent documents and elsewhere and a suitable complex can be selected from them and used in this invention.

Preferable phosphorescent dopants include complexes having a noble metal element such as Ir in the center, typically Ir(ppy)$_3$, complexes such as Ir(pq)$_2$(acac), Ir(piq)$_2$(acac), Ir(piq)$_3$, FIrpic, and complexes such as PtOEt$_3$, but are not limited thereto.

The content of the aforementioned phosphorescent dopant in the light emitting layer is preferably in the range of 1 wt % to 15 wt %.

Preferred Embodiments of the Invention

The structure of the organic electroluminescent device of this invention will be explained with reference to the drawing, but not limited thereto.

FIG. 1 is a schematic view showing an organic light emitting device according to an embodiment of the present invention. An organic light emitting device 100 includes a substrate 110, an anode 120, a hole injection layer 130, a hole transport layer 140, an emissive layer 150, an electron transport layer 160, an electron injection layer 170, and a cathode 180. The organic light emitting device 100 may be fabricated by depositing the layers described in order.

Figure 2:
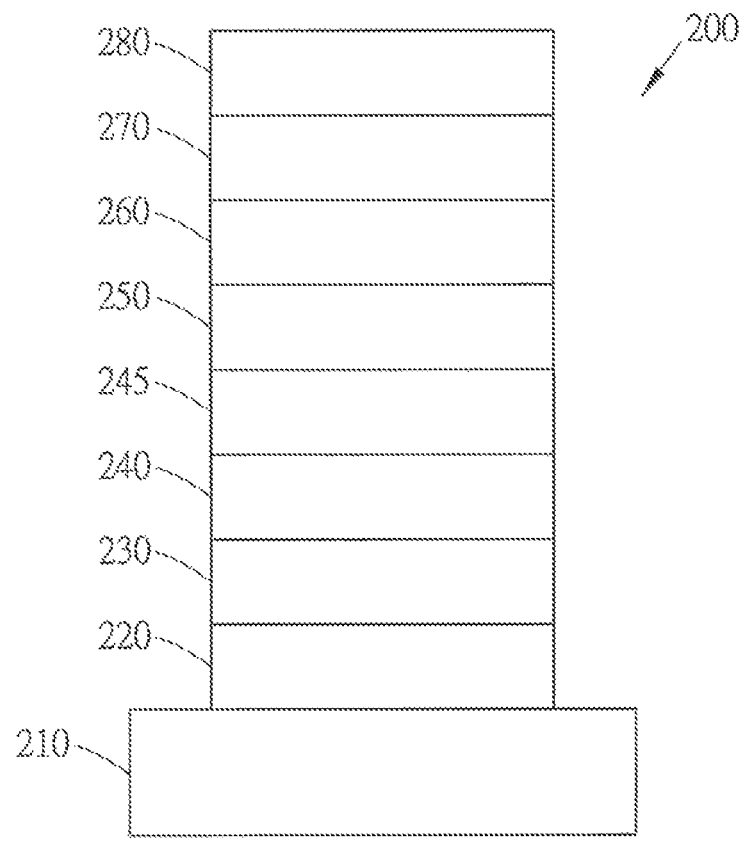
FIG. 2 is a cross-sectional view illustrating another example of an organic light emitting device according to another embodiment of the present invention.

FIG. 2 is a schematic view showing an organic light emitting device according to another embodiment of the present invention. An organic light emitting device 200 includes a substrate 210, an anode 220, a hole injection layer 230, a hole transport layer 240, an exciton blocking layer 245, a light emitting layer 250, an electron transport layer 260, an electron injection layer 270, and a cathode 280.

Figure 3:
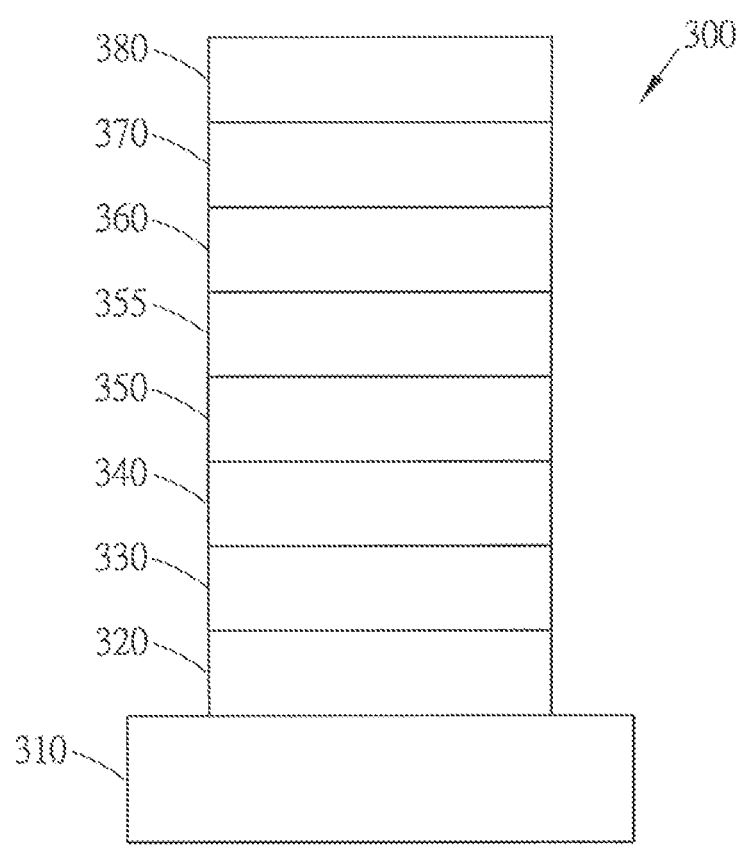
FIG. 3 is a cross-sectional view illustrating yet another example of an organic light emitting device according to another embodiment of the present invention.

FIG. 3 is a schematic view showing an organic light emitting device according to another embodiment of the present invention. An organic light emitting device 300 includes a substrate 310, an anode 320, a hole injection layer 330, a hole transport layer 340, a light emitting layer 350, an exciton blocking layer 355, an electron transport layer 360, an electron injection layer 370, and a cathode 380. It is possible to fabricate an organic light emitting device with a structure that is the reverse of the one shown in FIGS. 1-3. In this case of the reverse structure, a layer or layers may be added or omitted as needed.

Materials used in hole injection layer, hole transport layer, electron blocking layer, hole blocking layer, electron transport layer, electron injection layer may be selected from those reported in the literature cited elsewhere.

For example, an electron-transporting material forming the electron-transporting layer differs from the material forming the light emitting layer and has hole-transporting properties, so as to facilitate the hole mobility in the electron-transporting layer, and to prevent accumulation due to the difference in ionization potential between the light emitting layer and the electron-transporting layer can be prevented.

In addition, U.S. Pat. No. 5,844,363, which is incorporated by reference in its entirety, discloses a flexible and transparent substrate-anode combination. An example of a p-doped hole transport layer is m-MTDATA doped with $F_4$-TCNQ at a molar ratio of 50:1, as disclosed in US Patent Application Publication No. 20030230980, which is incorporated by reference in its entirety. An example of an n-doped electron transport layer is BPhen doped with Li at a molar ratio of 1:1, as disclosed in US Patent Application Publication No. 20030230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in U.S. Pat. No. 6,097,147 and US Patent Application Publication No. 20030230980, which are incorporated by reference in their entireties. Examples of injection layers are provided in US Patent Application Publication No. 20040174116, which is incorporated by reference in its entirety. A description of protective layers may be found in US Patent Application Publication No. 20040174116, which is incorporated by reference in its entirety.

Structures and materials not specifically described may also be used, such as OLEDs comprised of polymeric materials (PLEDs) such as disclosed in U.S. Pat. No. 5,247,190, which is incorporated by reference in its entirety. Further, OLEDs having a single organic layer may be used. OLEDs may be stacked as described in U.S. Pat. No. 5,707,745, which is incorporated by reference in its entirety.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102, which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with deposition methods such as ink-jet and OVJD. Certainly, other methods may be used. The materials to be deposited may be modified to make them compatible with a particular deposition method.

An organic electroluminescent device of this invention is applicable to a single device, a device with its structure arranged in array, or a device having the anode and the cathode arranged in an X-Y matrix. The present invention significantly improves luminous efficiency and driving stability of an organic electroluminescent device over the conventional devices, when used in combination of phosphorescent dopants in the light emitting layer, and furthermore the organic electroluminescent device of the present invention can perform better when applied to full-color or multicolor panels.

EXAMPLES

This invention will be described in more detail below with reference to the examples; however, it will not be limited to these examples and it can be reduced to practice in various modes unless such practice exceeds the substance of this invention.

9-acetyl-3-bromocarbazole 20 g of 3-bromocarbazole was converted to its acetyl derivative by refluxing with acetic anhydride (3 vol) with traces of conc. sulfuric acid. Aqueous workup yielded an off-white solid, which was then washed with n-hexane and dried under vacuum to obtain 23 g 9-acetyl-4-bromocarbazole, quantitatively.

9-acetyl-2-bromocarbazole and
9-acetyl-1-bromocarbazole 9-acetyl-2-bromocarbazole and 9-acetyl-1-bromocarbazole were synthesized according to the procedure of 9-acetyl-3-bromocarbazole.

4-bromo-p-terphenyl and 3-bromo-p-terphenyl 4-bromo-p-terphenyl and 3-bromo-p-terphenyl were synthesized according to the procedures given in Inorg. Chem. 2008, No. 47, p. 7035.

Synthesis Example 1

Synthesis of Compound 1-11

A mixture of 1.2 g of 9-acetyl-3-bromocarbazole and 2.2 g of N'-1-naphthyl-N,N-diphenyl-1,4-benzenediamine were stirred together in 20 ml N,N'-dimethylacetamide. To this was added 0.8 g of copper oxide and heated to 170° C. for 24 h. The reaction was quenched with water and the solid was filtered, washed with methanol, and dried under vacuum. The solid was then taken up for further deprotection using 0.6 g KOH with TI-IF (3 ml), methanol (6 ml) and water (6 ml) at reflux temperature. The reaction mixture was then extracted using ethyl acetate; and the organic layer was dried over anhydrous sodium sulfate and evaporated to dryness under vacuum. Subsequent silica gel column chromatography using toluene/hexane (½) as eluent, yielded 1.6 g of N-(9H-carbazol-3-yl)-N-(naphthalen-1-yl)-N',N'-diphenylbenzene-1,4-diamine.

The above obtained N-(9H-carbazol-3-yl)-N-(naphthalen-1-yl)-N',N'-diphenyl benzene-1,4-diamine (1.6 g) was dissolved in 30 ml of dry toluene under nitrogen. 1.3 g of 3-bromo-p-terphenyl 0.06 g of tris(dibenzylideneacetone) dipalladium, 0.05 g of tri-t-butylphosphine and 1.04 g of potassium orthophosphate were added and heated to reflux for 16 h. The product was precipitated by pouring the reaction mixture into water. The solid thus obtained was then washed with methanol and dried under vacuum to obtain 1.5 g of N-(naphthalen-1-yl)-N',N'-diphenyl-N-[9-(1,1':4',1"-terphenyl-3-yl)-9H-carbazol-3-yl]benzene-1,4-diamine, compound 1-11 (65%).

Compound 1-11 showed a melting point of 263° C. and a glass transition temperature of 146° C.

Figure 4:
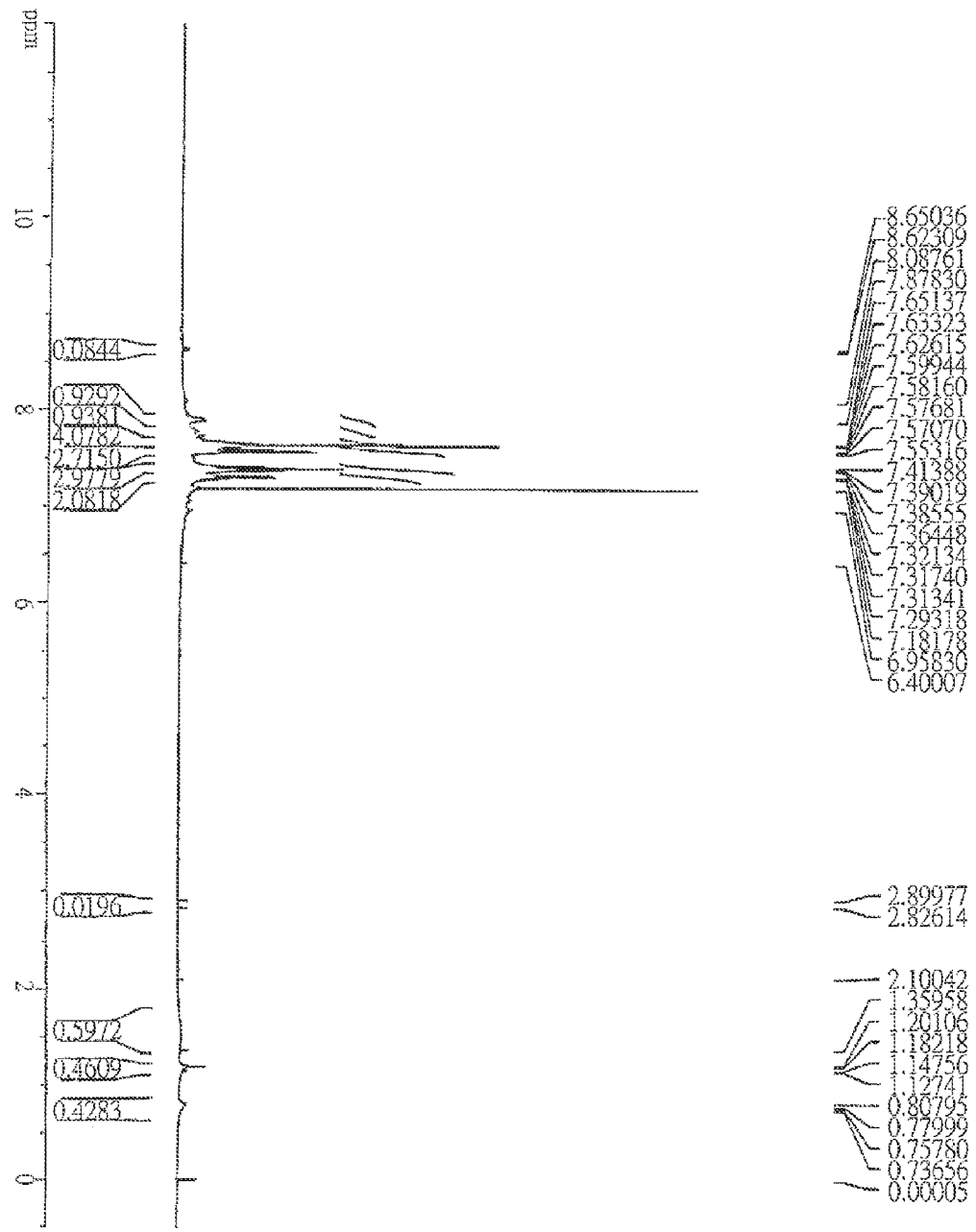
FIG. 4 shows the $^1$H-NMR spectrum of the compound No. 1-11 according to the present invention.

$^1$H-NMR is shown in FIG. 4. $^1$H NMR (CDCl$_3$, δ): 7.87 (m, 3H); 7.65 (m, 3H); 7.63 (m, 12H); 7.60 (m, 8H); 7.39 (m, 9H); 7.31 (m, 6H).

Synthesis Example 2

Synthesis of Compound 1-16

Indolo[2,3-a]carbazole (9.8 g) was dissolved in 150 ml of dry toluene under nitrogen. 12.9 g of 3-bromo-p-terphenyl, 0.65 g of tris(dibenzylideneacetone) dipalladium, 0.46 g of tri-t-butylphosphine and 40.3 g of potassium orthophosphate were added and heated to reflux for 16 h. After the completion of reaction, the reaction was quenched with water. The reaction mixture was then extracted using ethyl acetate; and the organic layer was dried over anhydrous sodium sulfate and evaporated to dryness under vacuum. Subsequent silica gel column chromatography using ethyl acetate/hexane (1:9) as eluent, yielded 12.6 g of N-(1,1':4',1"-terphenyl-3-yl) indolo[2,3-a]carbazole.

The above obtained N-(3,1:4',1"-terphenyl)indolo[2,3-a] carbazole (1.5 g) was dissolved in 30 ml of dry N,N'-dimethylformamide under nitrogen. 0.15 g of sodium hydride was added and stirred at room temperature for 1 h. A solution of 2-chloro-4,6-diphenyl-1,3,5-triazine (U-1, 1.0 g) in dry N,N'-dimethylformamide (10 ml) was then added to the reaction mixture. The reaction was further allowed to stir for 3 h. The product was precipitated by pouring the reaction mixture into water. The solid thus obtained was then washed with methanol and dried under vacuum to obtain 2.1 g of N-(4,6-diphenyl-1,3,5-triazin-2-yl)-N'-(1,1':4',1"-terphenyl-3-yl) indolo[2,3-a]carbazole, compound 1-16 (73%).

Compound 1-16 showed a melting point of 263° C. and a glass transition temperature of 146° C.

Figure 5:
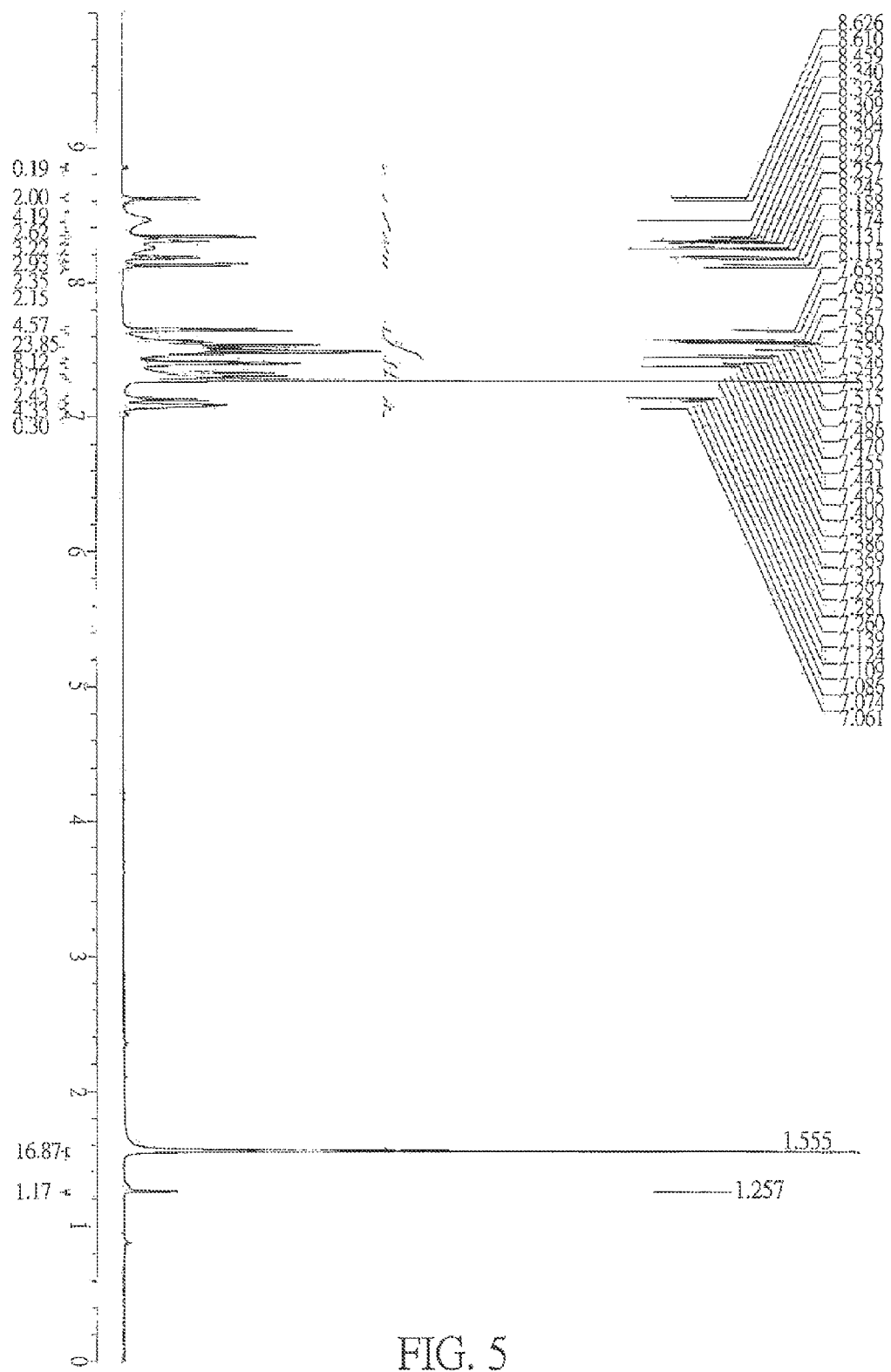
FIG. 5 shows the $^1$H-NMR spectrum of the compound No. 1-16 according to the present invention.

$^1$H-NMR is shown in FIG. 5. $^1$H NMR (CDCl$_3$, δ): 8.62 (d, 1H); 8.33 (d, 1H); 8.30 (m, 2H); 8.18 (d, 1H); 8.12 (d, 1H); 7.65 (d, 2H); 7.58-7.44 (m, 12H); 7.41-7.38 (m, 4H); 7.32-7.28 (m, 4H); 7.14-7.11 (m, 1H); 7.09-7.06 (m, 2H).

Synthesis Example 3

Synthesis of Compound 1-27

The above obtained N-(1,1':4',1"-terphenyl-3-yl)indolo[2,3-a]carbazole (2.9 g) was dissolved in 30 ml of DMSO under nitrogen. Potassium hydroxide (1.0 g), tetra-n-butylammonium hydroxide (0.3 g) and bromoethane (1.3 g) were added and stirred at room temperature for 3 h. The product was precipitated by pouring the reaction mixture into water. The solid thus obtained was then washed with n-hexane and dried under vacuum to obtain 1.5 g of N-ethyl-N'-(1,1':4',1"-terphenyl-3-yl)-indolo[2,3-c]carbazole, compound 1-27 (49%).

Compound 1-27 showed a melting point of 207° C. and a glass transition temperature of 107° C.

Figure 6:
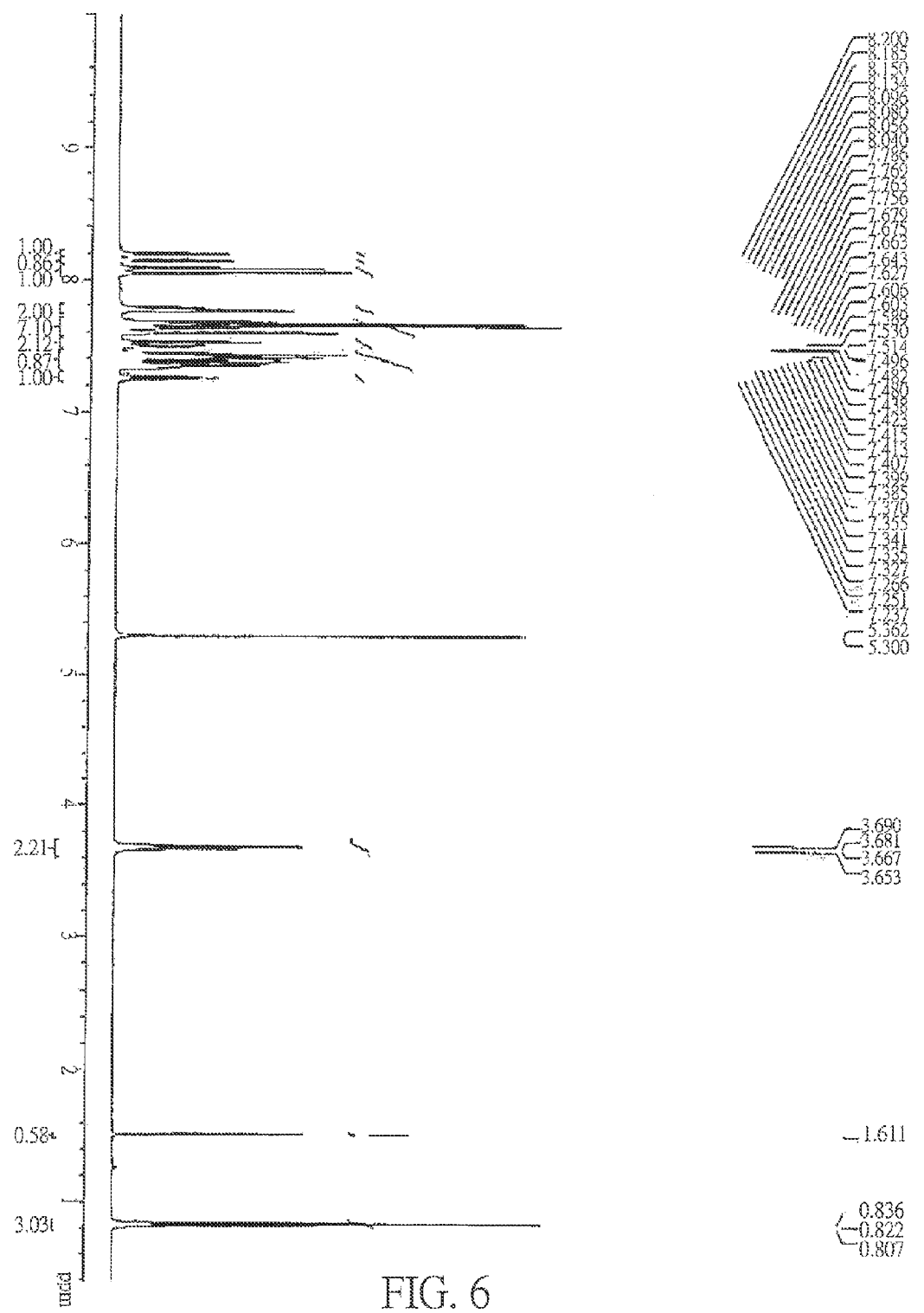
FIG. 6 shows the $^1$H-NMR spectrum of the compound No. 1-27 according to the present invention.

$^1$H-NMR is shown in FIG. 6. $^1$H NMR (CD$_2$Cl$_2$, δ): 8.19 (d, 1H); 8.14 (d, 1H); 8.06 (q, H); 7.78-7.75 (m, 2H); 7.67 (s, 1H); 7.67-7.02 (m, 4H); 7.59 (d, 2H); 7.52 (d, 1H); 7.49-7.48 (m, 1H); 7.43-7.32 (m, 8H); 7.25 (t, 1H); 3.07 (q, 2H); 0.82 (t, 3H).

Synthesis Example 4

Synthesis of Compound 1-30

A mixture of 1.2 g of 9-acetyl-3-bromocarbazole and 1.2 g of di-p-tolylamine were stirred together in 20 ml N,N'-dimethylacetamide. To this was added 0.8 g of copper oxide and heated to 170° C. for 24 h. The reaction was quenched with water and the solid was filtered, washed with methanol, and dried under vacuum. The solid was then taken up for further deprotection using 0.6 g KOH with THF (3 ml), methanol (6 ml) and water (6 ml) at reflux temperature. The reaction mixture was then extracted using ethyl acetate; and the organic layer was dried over anhydrous sodium sulfate and evaporated to dryness under vacuum. Subsequent silica gel column chromatography using toluene/hexane (½) as eluent, yielded 1.2 g of 3-(N,N-di-p-tolylamino)-9H-carbazole.

The above obtained 3-(N,N-di-p-tolylamino)-9H-carbazole (1.2 g) was dissolved in 30 ml of dry toluene under nitrogen. 1.3 g of 3-bromo-p-terphenyl, 0.06 g of tris(dibenzylideneacetone)dipalladium, 0.05 g of tri-t-butylphosphine and 1.04 g of potassium orthophosphate were added and heated to reflux for 16 h. The product was precipitated by pouring the reaction mixture into water. The solid thus obtained was then washed with methanol and dried under vacuum to obtain 1.8 g of 3-(N,N-di-p-tolylamino)-9-(1,1':4',1"-terphenyl-3-yl)-carbazole, compound 1-30 (73%).

Figure 7:
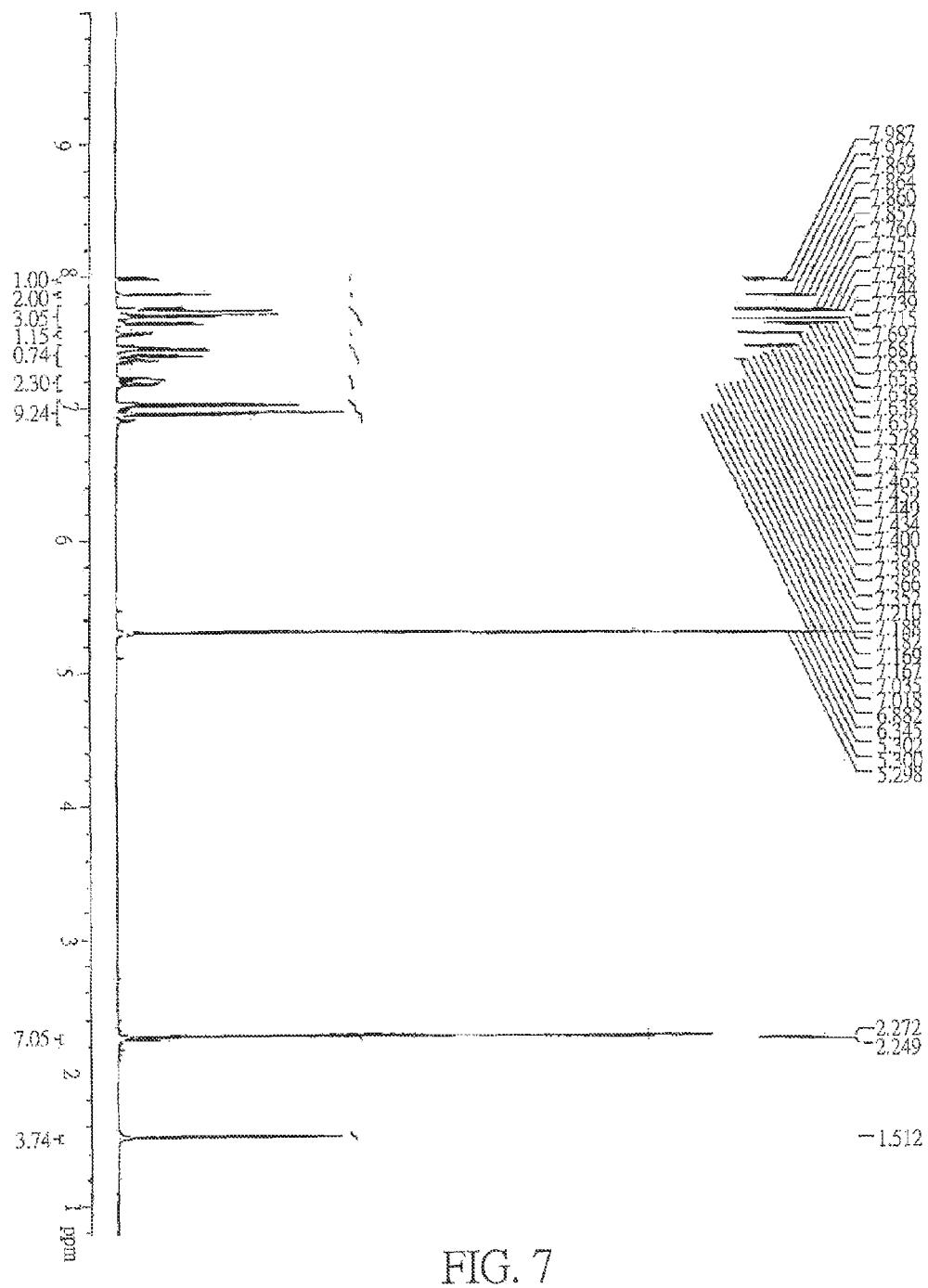
FIG. 7 shows the $^1$H-NMR spectrum of the compound No. 1-30 according to the present invention.

$^1$H-NMR is shown in FIG. 7. $^1$H NMR (CD$_2$Cl$_2$, δ): 7.98 (d, 1H); 7.87-7.85 (m, 2H); 7.76-7.43 (m, 8H); 7.58-7.55 (m, 1H); 7.48-7.33 (m, 7H); 7.21 (t, 1H); 7.17 (dd, 1H); 7.04-6.89 (m, 6H); 2.27 (s, 6H).

Synthesis Example 5

Synthesis of Compound 1-31

A mixture of 1.2 g of 9-acetyl-3-bromocarbazole and 2.2 g of bis-(4-biphenylamine) were stirred together in 20 ml N,N'-dimethylacetamide. To this was added 0.8 g of copper oxide and heated to 170° C. for 24 h. The reaction was quenched with water and the solid was filtered, washed with methanol, and dried under vacuum. The solid was then taken up for further deprotection using 0.6 g KOH with THF (3 ml), methanol (6 ml) and water (6 ml) at reflux temperature. The reaction mixture was then extracted using ethyl acetate; and the organic layer was dried over anhydrous sodium sulfate and evaporated to dryness under vacuum. Subsequent silica gel column chromatography using toluene/hexane (½) as eluent, yielded 2.2 g of 3-(N,N-bis-4-biphenylamino)-9H-carbazole.

The above obtained 3-(N,N-bis-4-biphenylamino)-9H-carbazole (1.2 g) was dissolved in 30 ml of dry toluene under nitrogen. 1.3 g of 3-bromo-p-terphenyl, 0.06 g of tris(dibenzylideneacetone)dipalladium, 0.05 g of tri-t-butylphosphine and 1.04 g of potassium orthophosphate were added and heated to reflux for 16 h. The product was precipitated by pouring the reaction mixture into water. The solid thus obtained was then washed with methanol and dried under vacuum to obtain 1.8 g of 3-(N,N-bis-4-biphenylamino)-9-(1,1':4',1''-terphenyl-3-yl)-carbazole, compound 1-31 (73%).

Compound 1-31 showed a melting point of 257° C. and a glass transition temperature of 113° C.

Figure 8:
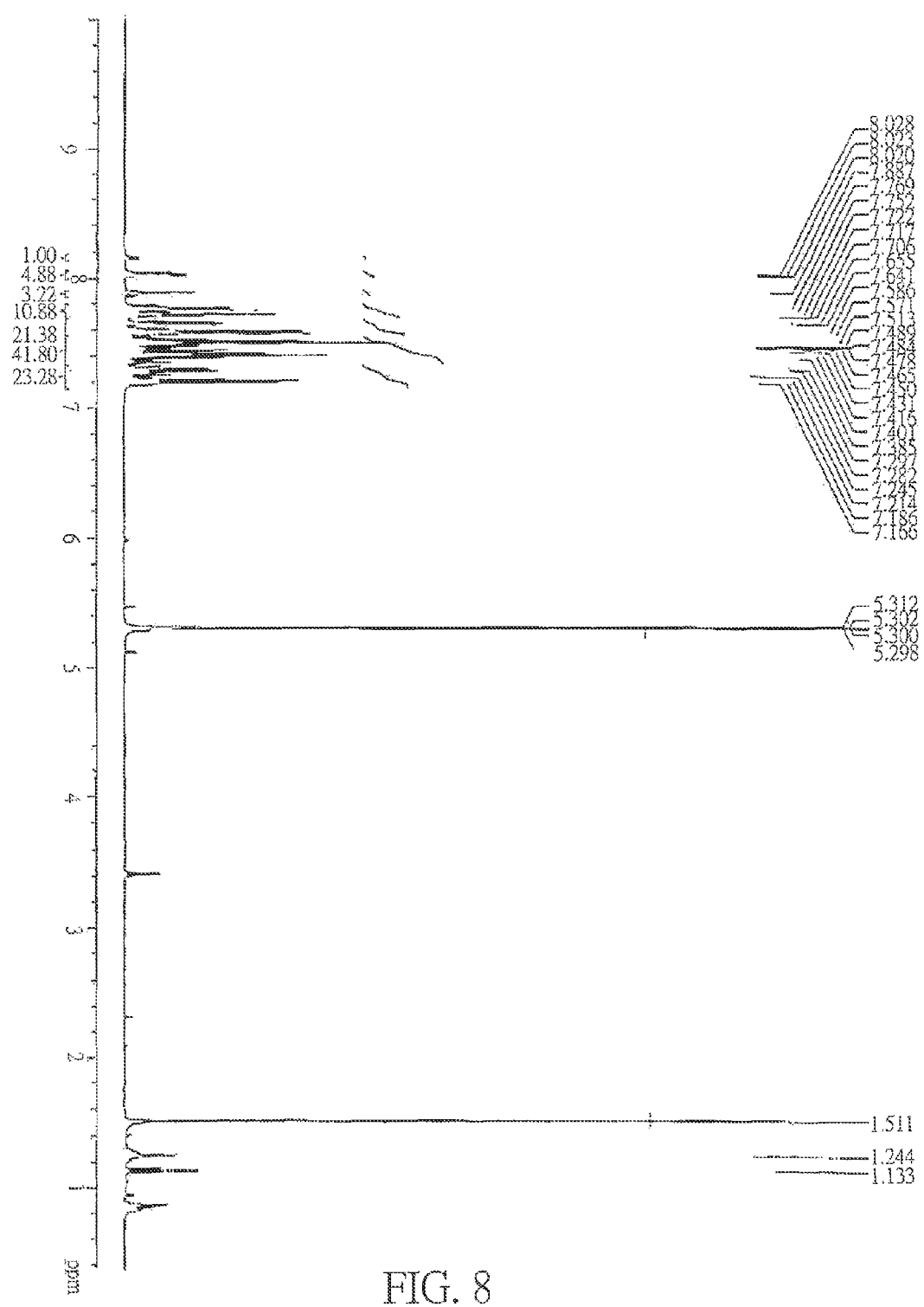
FIG. 8 shows the $^1$H-NMR spectrum of the compound No. 1-31 according to the present invention.
Figure 9:
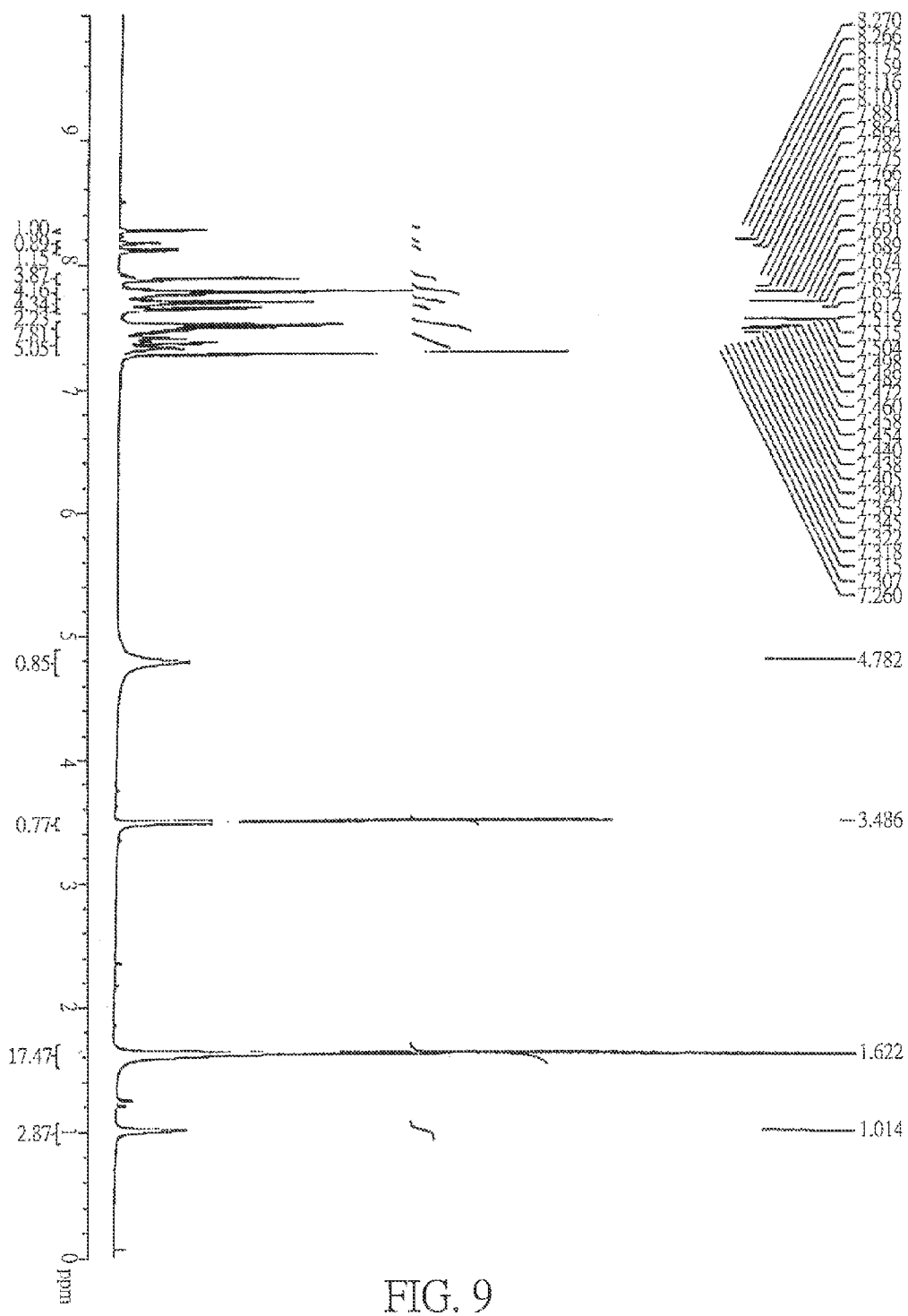
FIG. 9 shows the $^1$H-NMR spectrum of the compound No. 1-32 according to the present invention.

$^1$H-NMR is shown in FIG. 8. $^1$H NMR (CD$_2$Cl$_2$, δ): 8.04-8.02 (m, 2H); 7.89 (s, 1H); 7.78-7.70 (m, 6H); 7.65-7.57 (m, 7H); 7.54-7.35 (m, 14H); 7.32-7.17 (m, 8H).

Example 1

Fabrication of Organic Electroluminescent Device

Prior to use, the substrate was degreased with solvents and cleaned in a UV ozone before it was loaded into the evaporation system. The substrate was then transferred into a vacuum deposition chamber for deposition of all other layers on top of the substrate. The following layers were deposited in the following sequence, as shown in FIG. 2, by evaporation from a heated boat under a vacuum of approximately 10$^{-6}$ Torr:

a) a hole injection layer, EHI609 (from E-ray optoelectronics Tech Co Ltd, Taiwan);

b) a hole transport layer, 7 nm thick, including N,N'-di-1-naphthyl-N,N'-diphenyl-4,4'-diaminobiphenyl (NPB);

c) an exciton-blocking layer, 5 nm thick, including 4,4',4''-tris(carbazol-9-yl)-triphenylamine (TCTA);

d) a light emitting layer, 30 nm thick, including compound 1-16 doped with 7% Ir(ppy)$_3$ by volume;

e) an electron transport layer, 30 nm thick, including tris-(8-hydroxyquinoline) aluminum (Alq$_3$);

f) an electron injection layer, 1 nm thick, LiF; and g) a cathode: approximately 150 nm thick, including Al.

The structure of the organic electroluminescent device may be denoted as: ITO/EHI609 (70 nm)/NPB (7 nm)/TCTA (5 nm)/compound 1-1:7% Ir(ppy)$_3$ (30 nm)/Alq$_3$ (30 nm)/LiF (1 nm)/Al (150 nm)

Figure 10:
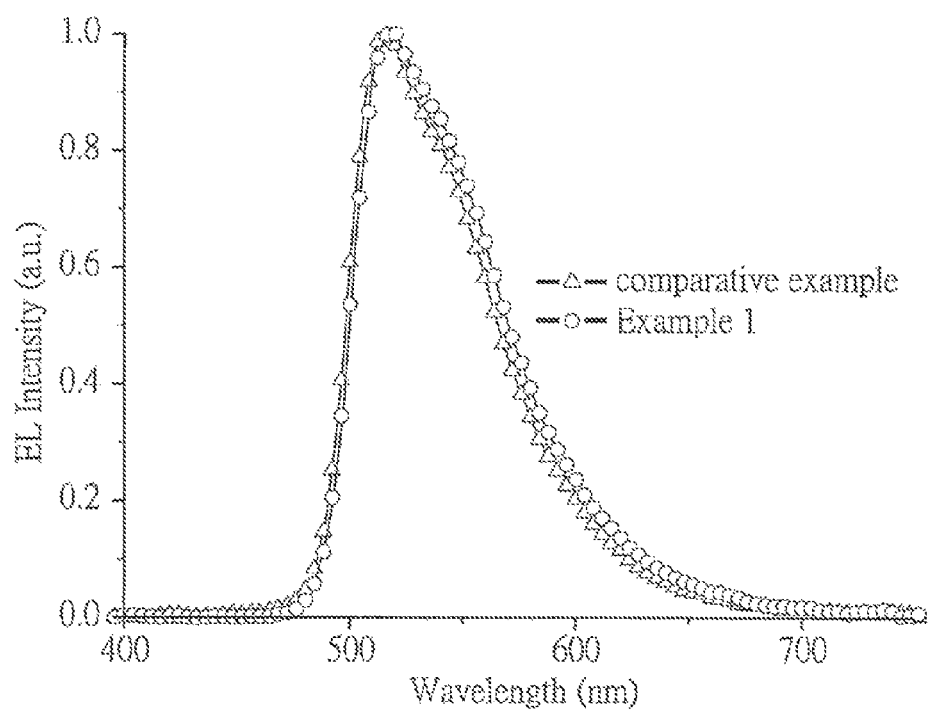
FIG. 10 shows the electroluminescent spectrum of the organic electroluminescent devices according to the present invention.

After the deposition of these layers, the device was transferred from the deposition chamber into a dry box for encapsulation, and subsequently encapsulated by using a UV-curable epoxy, and a glass lid containing a moisture getter. The organic electroluminescent device has an emission area of 3 mm$^2$. The organic electroluminescent device thus obtained was connected to an outside power source, and upon applying direct current voltage, emission of light with the characteristics shown in Table 2 were confirmed. The electroluminescent spectrum of this device is shown in FIG. 10.

The EL characteristics of all the fabricated devices in the present invention were evaluated using a constant current source (KEITHLEY 2400 Source Meter, made by Keithley Instruments, Inc., Cleveland, Ohio) and a photometer (PHOTO RESEARCH SpectraScan PR 650, made by Photo Research, Inc., Chatsworth, Calif.) at room temperature.

Operational lifetime (or stability) of the devices were tested at the room temperature and at an initial luminance of 10,000 cd/m$^2$ by driving a constant current through the devices. The color was reported using Commission Internationale de l'Eclairage (CIE) coordinates.

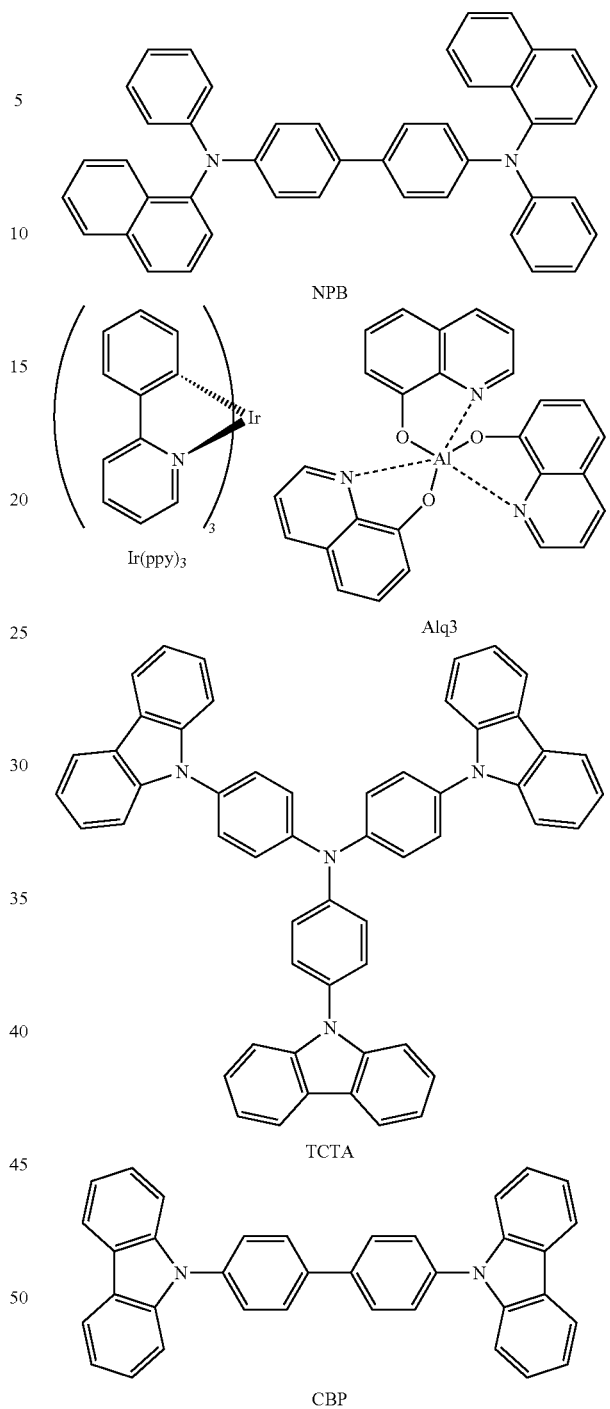

NPB

Ir(ppy)$_3$

Alq3

TCTA

CBP

Comparative Example

Fabrication of Organic Electroluminescent Device

An organic phosphorescent electroluminescent device was fabricated as a structure similar to the layer structure as example 1 except that CBP was used in place of the compound 1-16 in the light emitting layer. The structure of the organic phosphorescent electroluminescent device may be denoted as: ITO/EHI609 (70 nm)/NPB (7 nm)/TCTA (5 nm)/CBP:7% Ir(ppy)$_3$ (30 nm)/Alq$_3$ (30 nm)/LiF (1 nm)/Al (150 nm).

Figure 11:
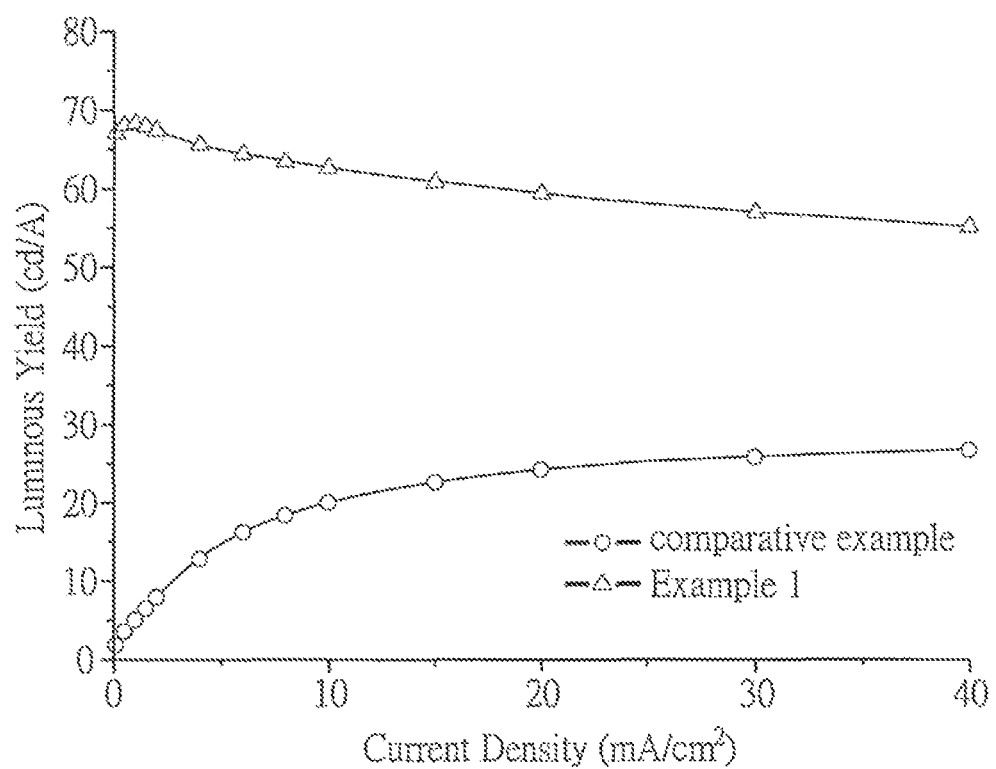
FIG. 11 shows the plot of luminance against current density of the electroluminescent devices according to the present invention.
Figure 12:
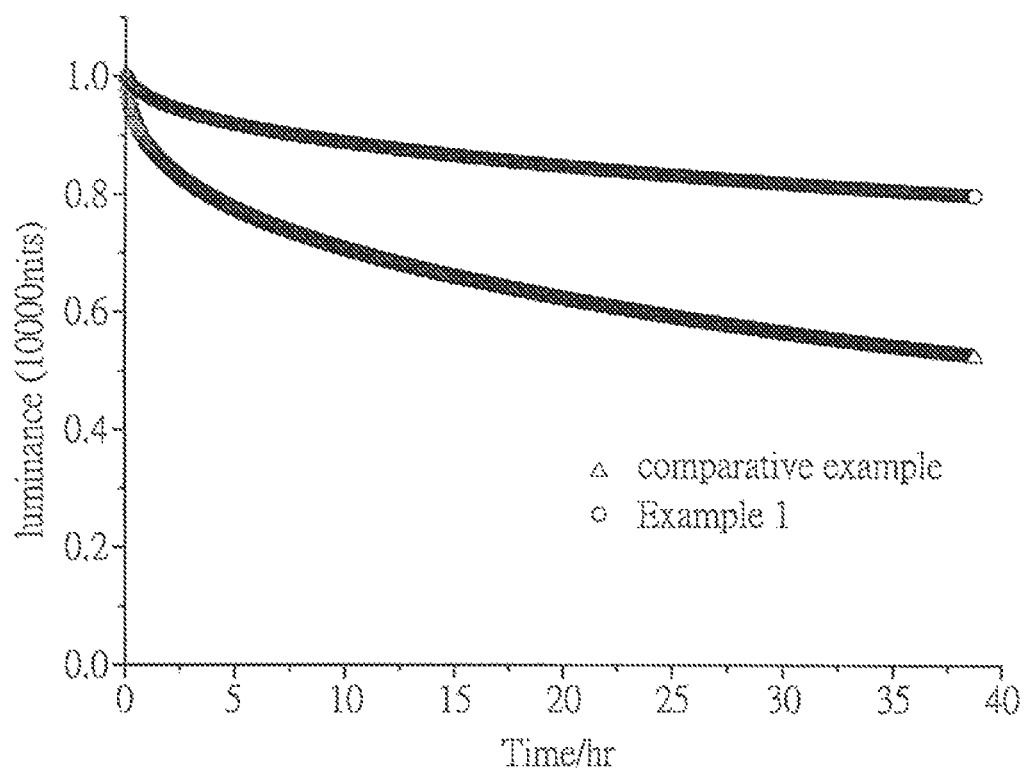
FIG. 12 shows the plot of luminance against time of the electroluminescent devices according to the present invention

The peak wavelength of emitted light, maximum luminous efficiency, and driving voltage and lifetime stability ($T_{80}$ at 10000 nits) of the organic electroluminescent devices fabricated in the examples are shown in Table 2. A plot of current density vs luminance is shown in FIG. 11 and a plot of luminance vs time at an initial luminance of 10000 nits is shown in FIG. 12.

TABLE 2

|  | Peak wavelength (nm) | Max. luminous efficiency (cd/A) @ 10 mA/cm$^2$ | Driving voltage (V) | $T_{80}$ @ 10000 nits |
|---|---|---|---|---|
| Example 1 | 520 | 62.58 | 5.62 | 38 h |
| Comparative Example | 516 | 20.00 | 8.35 | 3.7 h |

The invention shall not be limited to the above described embodiments, methods and examples.

INDUSTRIAL APPLICABILITY

As described above in detail, the organic electroluminescent device having the material for the organic electroluminescent device of the present invention has high luminous efficiency, high thermal stability, sufficiently low driving voltage and long lifetime.

Therefore, the organic electroluminescent device of this invention is applicable to flat panel displays, mobile phone displays, light sources utilizing the characteristics of planar light emitters, sign-boards and has a high technical value.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

The invention claimed is:
1. A carbazole derivative of formula (I) for an organic electroluminescent device:

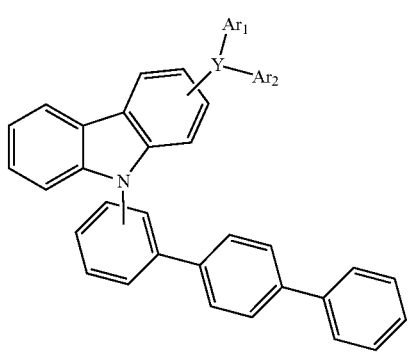

(I)

wherein Y represents one selected from N, O, P, S, a bicyclic heterocyclic ring fused with the carbazole, and a tricyclic heterocyclic ring;

Ar$_1$ and Ar$_2$ are each independently selected from the group consisting of H, alkyl, phenyl, biphenylyl, naphthalenyl, terphenyl,

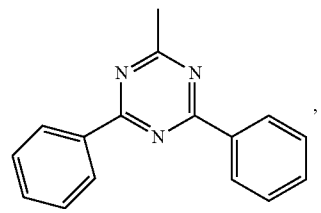 [SMILES: Cc1nc(-c2ccccc2)nc(-c2ccccc2)n1]

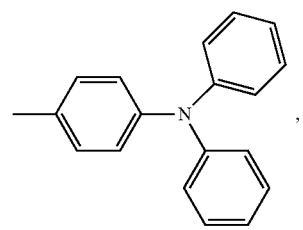

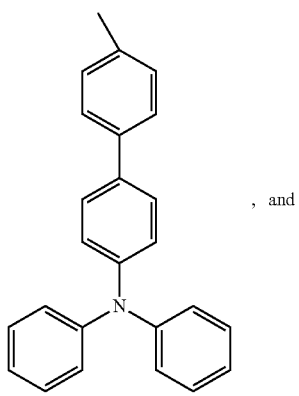

, and

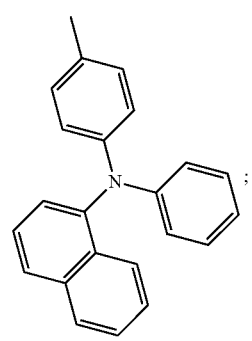

;

wherein Ar$_1$ and Ar$_2$ are each independently and optionally substituted by a substituent selected from the group consisting of alkyl, phenyl, alkoxy and

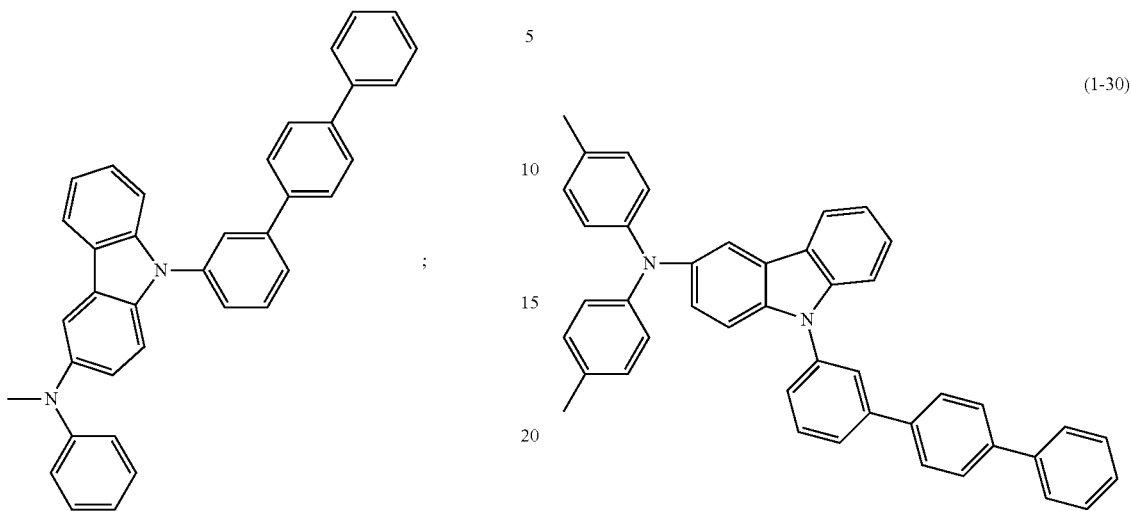

when Y represents N, $Ar_1$ is selected from the group consisting of phenyl, biphenylyl, naphthalenyl and terphenyl, and $Ar_2$ represents wherein $Ar_1$ and $Ar_2$ are each independently and optionally substituted by alkyl, or when Y represents N, $Ar_1$ and $Ar_2$ represents phenyl and biphenylyl respectively, and $Ar_2$ is substituted by or the carbazole derivative is one of compounds represented by formulas (1-30) and (1-31):

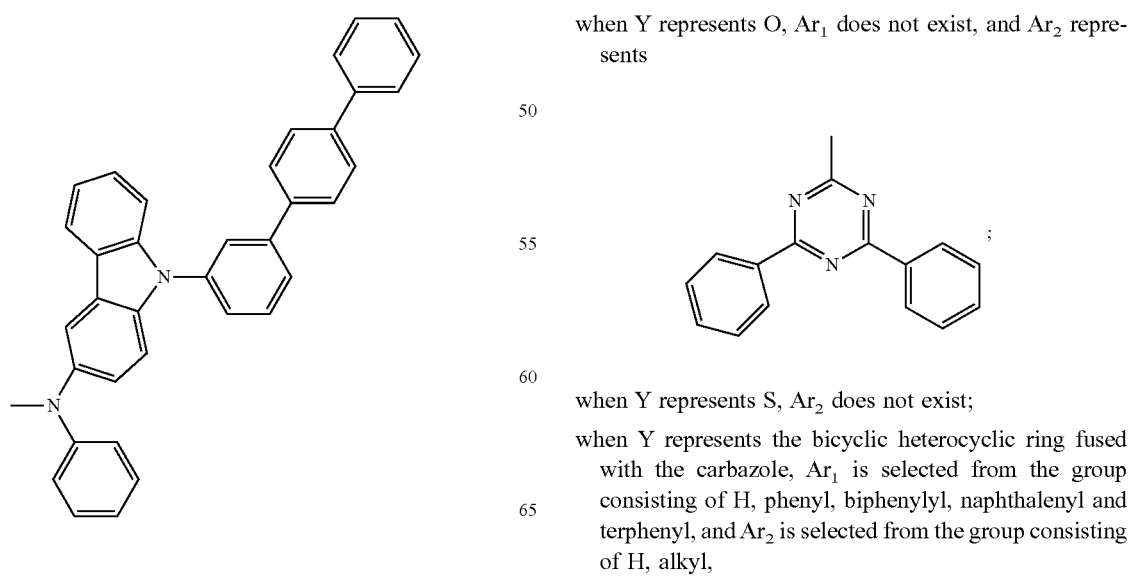

when Y represents O, $Ar_1$ does not exist, and $Ar_2$ represents when Y represents S, $Ar_2$ does not exist;

when Y represents the bicyclic heterocyclic ring fused with the carbazole, $Ar_1$ is selected from the group consisting of H, phenyl, biphenylyl, naphthalenyl and terphenyl, and $Ar_2$ is selected from the group consisting of H, alkyl,

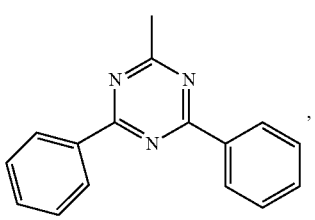 [SMILES: Cc1nc(-c2ccccc2)nc(-c2ccccc2)n1],

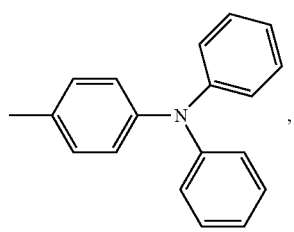,

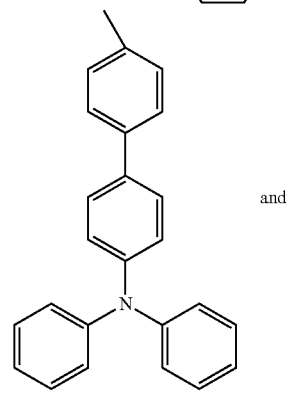 and

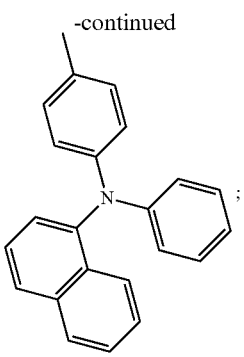;

wherein Ar₁ and Ar₂ are each independently and optionally substituted by a substituent selected from the group consisting of alkyl, phenyl and alkoxy; and when Y represents a tricyclic heterocyclic ring, Ar₁ represents H, and Ar₂ represents

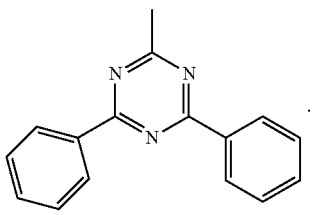 [SMILES: Cc1nc(-c2ccccc2)nc(-c2ccccc2)n1].

2. The carbazole derivative of claim 1, wherein Y represents a bicyclic heterocyclic ring fused with the carbazole.

3. The carbazole derivative of claim 1, being one of compounds represented by the following formulas:

(1-1)

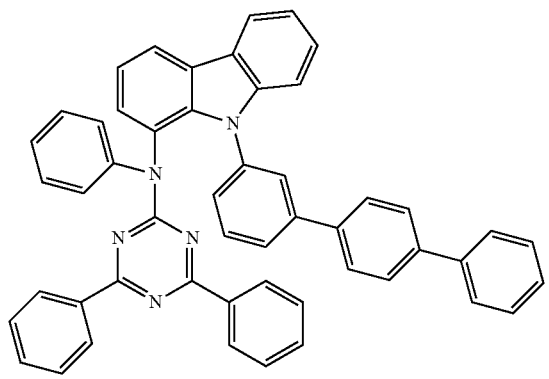

(1-2)

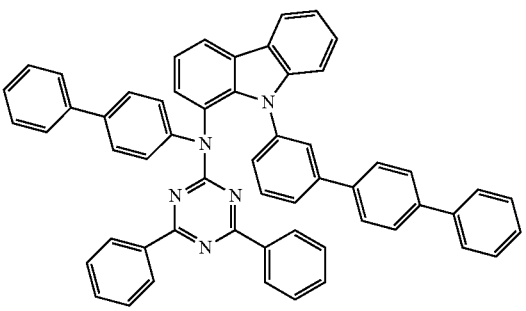

(1-3)

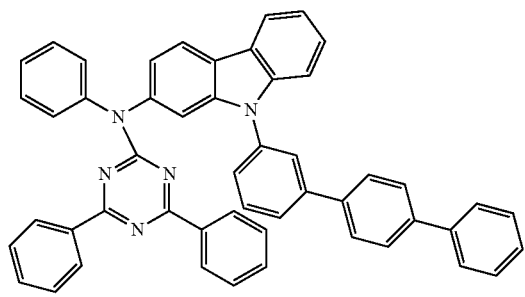

(1-4)

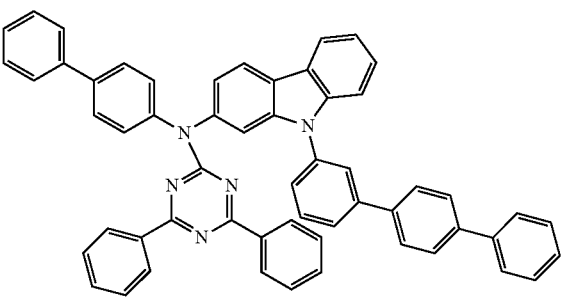

-continued
(1-5)
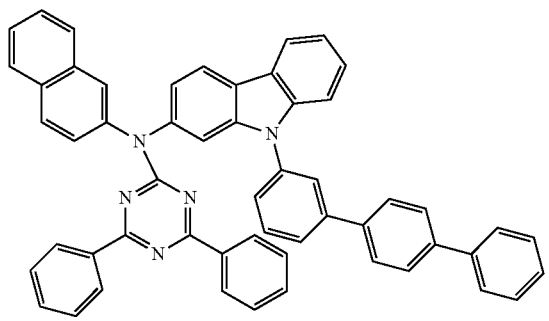
(1-6)
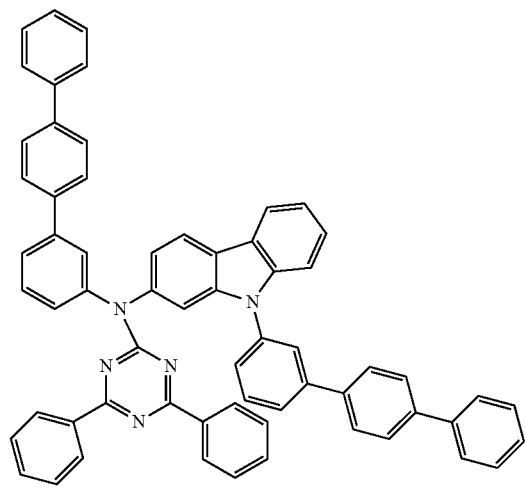
(1-7)
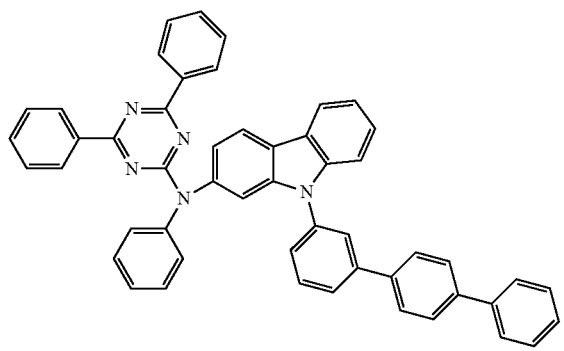
(1-8)
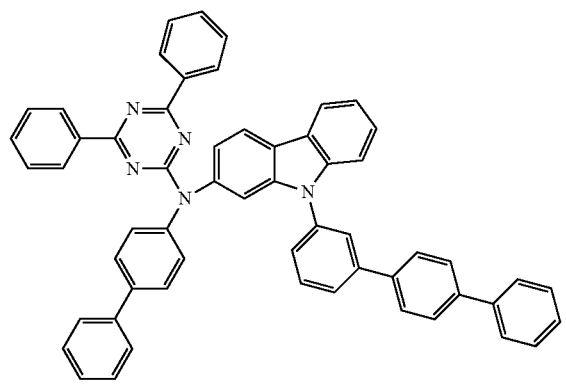
(1-9)
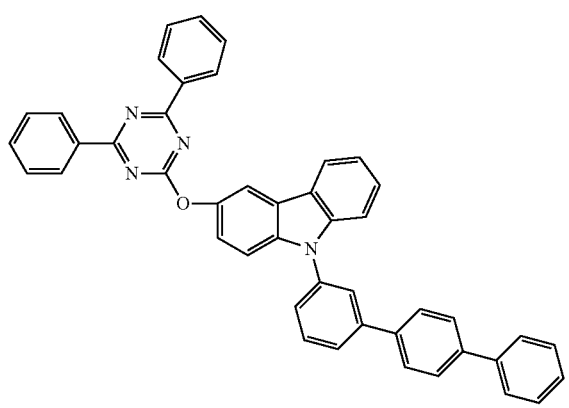
(1-10)
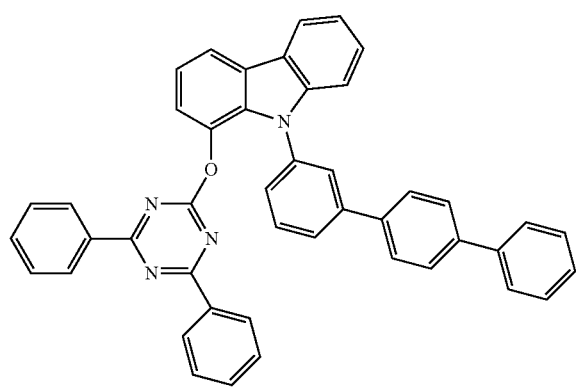

-continued
(1-12)
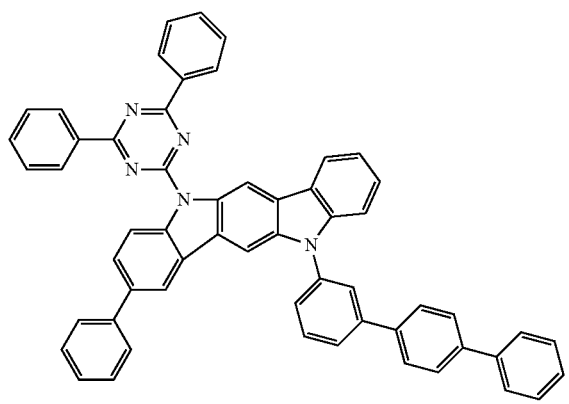
(1-16)
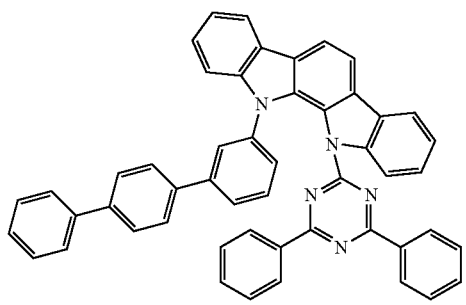
(1-17)
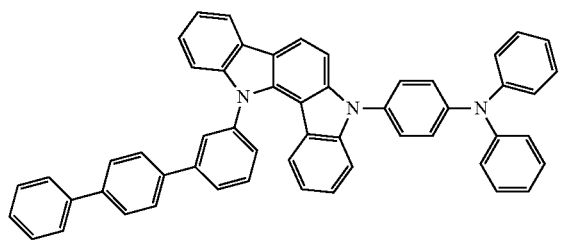
(1-18)
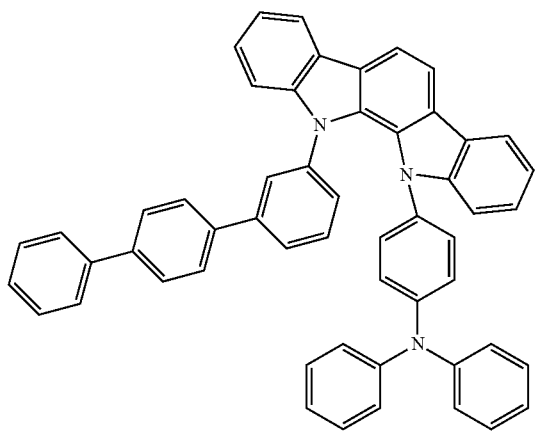
(1-19)
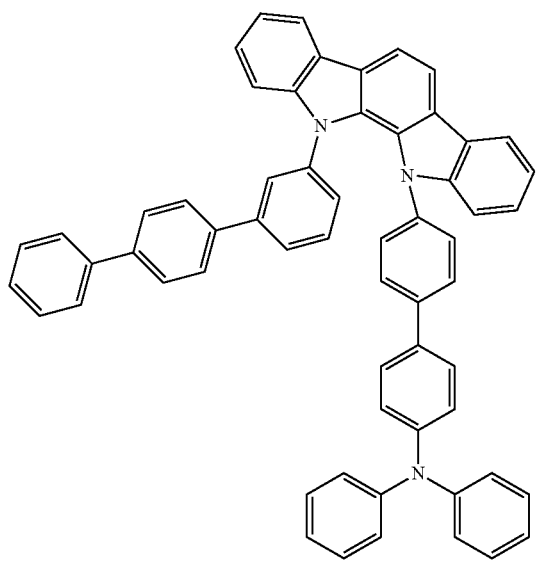
(1-20)
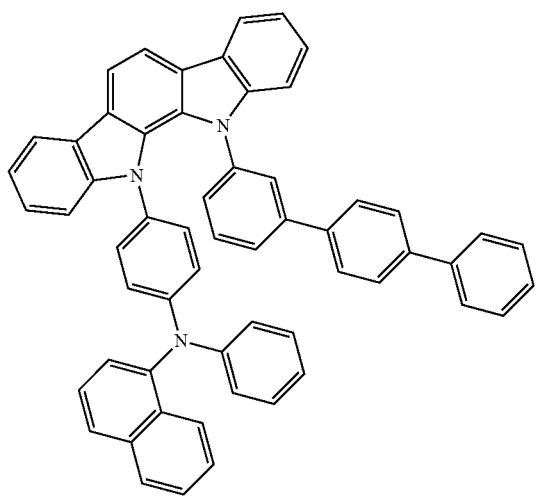

-continued
(1-21)
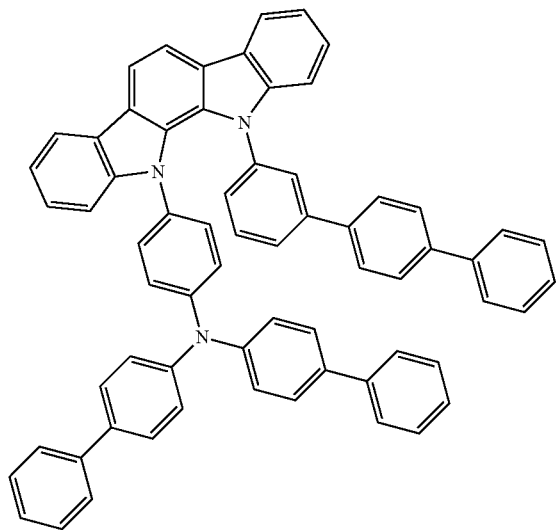
(1-22)
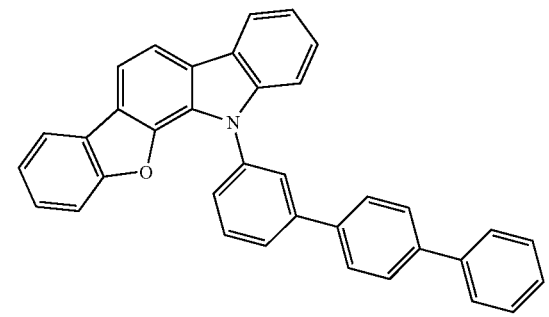
(1-23)
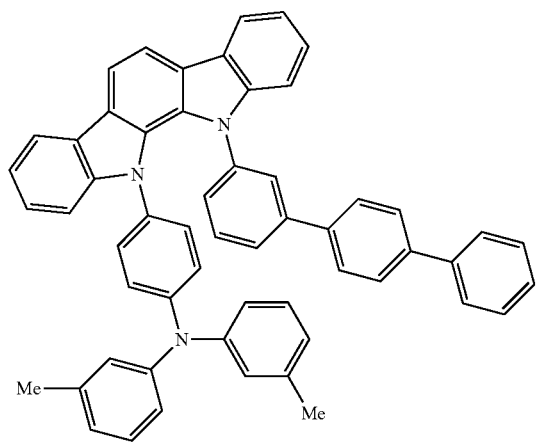
(1-24)
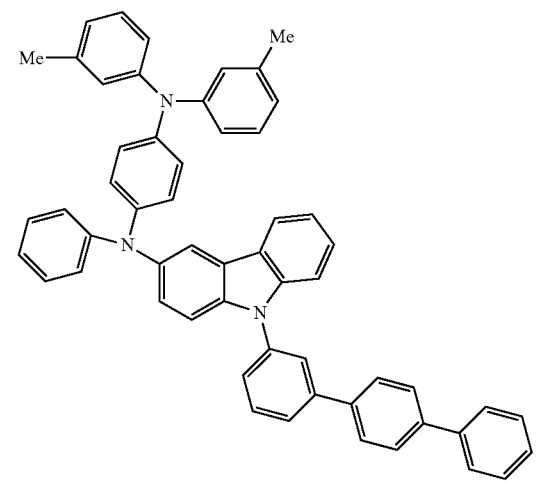
(1-25)
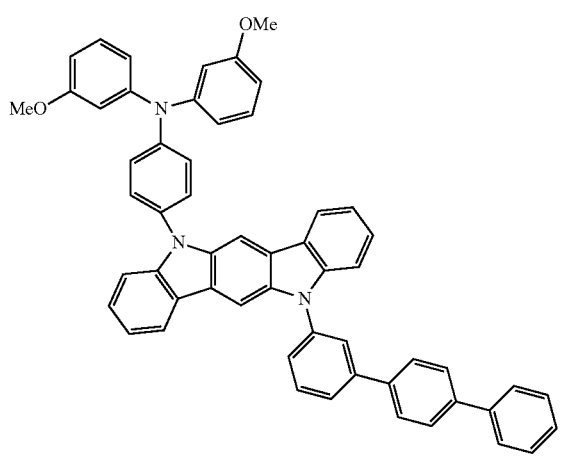
(1-27)
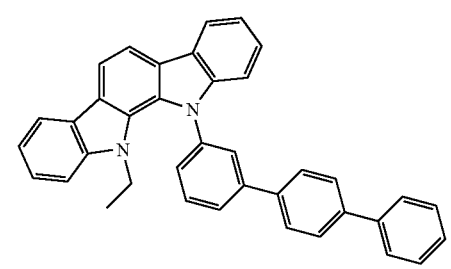

(1-28)
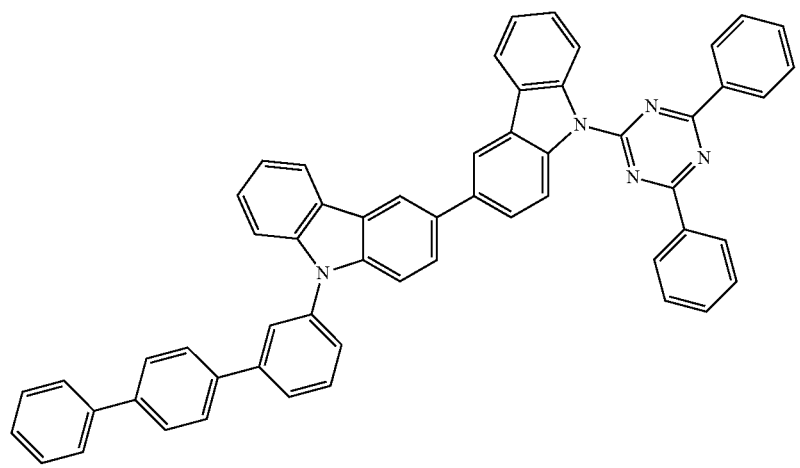
(1-29)
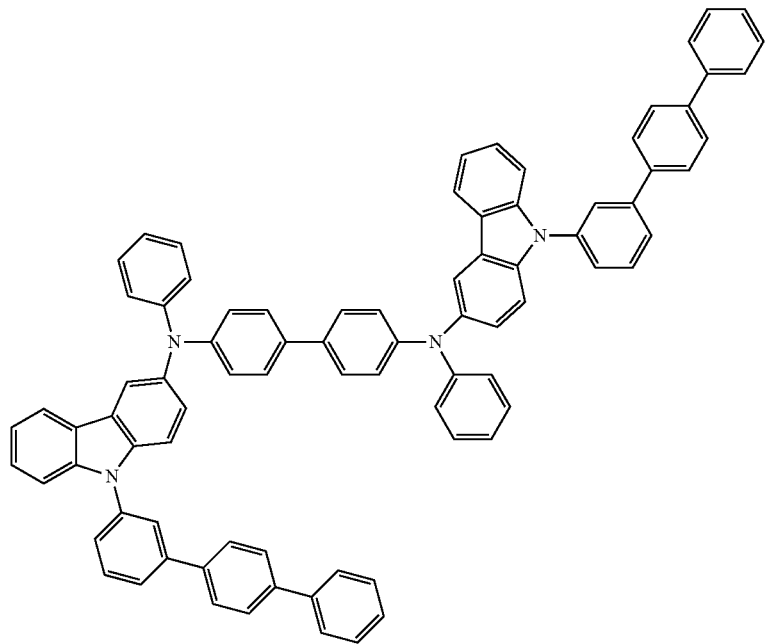
(1-30)
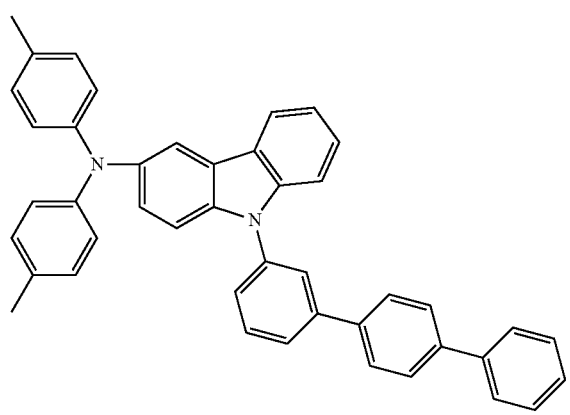
(1-31)
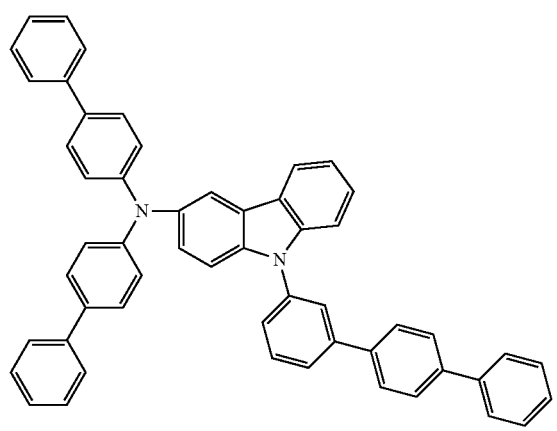

(1-32)

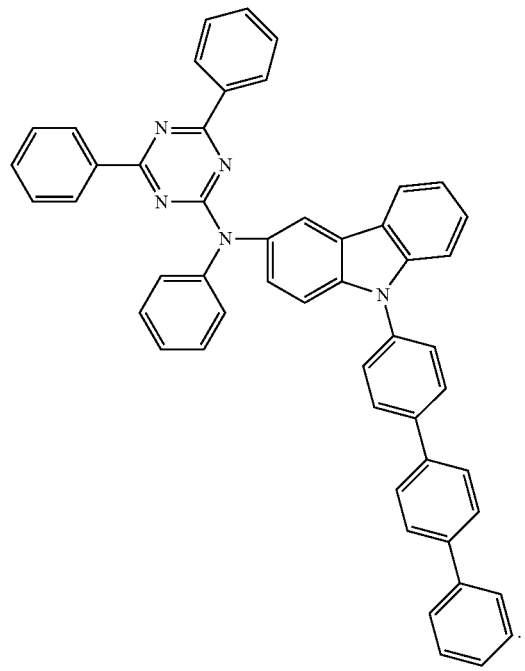

4. An organic electroluminescent device, comprising: a carbazole derivative of claim 1 or 3.

5. The organic electroluminescent device of claim 4, further comprising a light emitting layer containing a phosphorescent dopant and at least one compound of the carbazole derivative of claim 1 or 3.

6. The organic electroluminescent device of claim 5, wherein the phosphorescent dopant is an organic metal complex comprising at least one metal selected from the group consisting of ruthenium, rhodium, palladium, silver, rhenium, osmium, iridium, platinum and gold.

7. The organic electroluminescent device of claim 5, wherein the phosphorescent dopant is one of $Ir(ppy)_3$, $Ir(pq)_2(acac)$, $Ir(piq)_2(acac)$, $Ir(piq)_3$, FIrpic, and $PtOEt_3$.

8. The organic electroluminescent device of claim 5, wherein the content of the phosphorescent dopant in the light emitting layer is in the range of 1% by volume to 15% by volume based on the total content of the light emitting layer.

9. The organic electroluminescent device of claim 4, further comprising a hole transporting layer containing at least one compound of the carbazole derivative of claim 1 or 3.

10. The organic electroluminescent device of claim 4, further comprising an electron transporting layer containing at least one compound of the carbazole derivative of claim 1 or 3.

11. The organic electroluminescent device of claim 4, further comprising a hole block layer; and an electron block layer, wherein one of the hole block layer and the electron block layer contains at least one compound of the carbazole derivative of claim 1 or 3.

12. The organic electroluminescent device of claim 4, further comprising:
a substrate;
an electrode; and
a sandwich structure formed between the substrate and electrode, wherein said sandwich structure has a hole transporting layer, an electron transporting layer, and a light emitting layer sandwiched between the hole transporting layer and electron transporting layer.

13. The organic electroluminescent device of claim 12, wherein one of the hole transporting layer, electron transporting layer and light emitting layer contains at least one compound of the carbazole derivative of claim 1 or 3.

14. A method for forming an organic electroluminescent device, comprising:
forming an hole injection layer on a substrate;
forming an hole transport layer on the hole injecting layer;
forming an light emitting layer on the hole transport layer having a phosphorescent dopant and at least one compound of the carbazole derivative of claim 1 or 3;
forming an electron transporting layer on the light emitting layer;
forming an electron injection layer on the electron transporting layer; and
forming an electrode on the electron injection layer.

15. The method of claim 14, wherein the phosphorescent dopant is an organic metal complex comprising at least one metal selected from the group consisting of ruthenium, rhodium, palladium, silver, rhenium, osmium, iridium, platinum and gold.

16. The method of claim 14, wherein the phosphorescent dopant is one of $Ir(ppy)_3$, $Ir(pq)_2(acac)$, $Ir(piq)_2(acac)$, $Ir(piq)_3$, FIrpic, and $PtOEt_3$.

17. The method of claim 14, wherein the content of the phosphorescent dopant in the light emitting layer is in the range of 1 wt % to 15 wt %.

18. The method of claim 14, wherein the electrode is a cathode.

* * * * *

UNITED STATES PATENT AND TRADEMARK OFFICE
CERTIFICATE OF CORRECTION

PATENT NO. : 9,450,192 B2  Page 1 of 1
APPLICATION NO. : 13/310899
DATED : September 20, 2016
INVENTOR(S) : Balaganesan et al.

It is certified that error appears in the above-identified patent and that said Letters Patent is hereby corrected as shown below:

Item (73), the Assignee, reads:
E-RAY OPTOELECTRONICS TECHNOLOGY, Chung-Li (TW)

It should read:
E-RAY OPTOELECTRONICS TECHNOLOGY CO., Chung-Li (TW)

Signed and Sealed this
Sixteenth Day of May, 2017

Michelle K. Lee
*Director of the United States Patent and Trademark Office*